(12) United States Patent
Beckman et al.

(10) Patent No.: US 8,853,452 B2
(45) Date of Patent: Oct. 7, 2014

(54) COMPOUNDS, THEIR SYNTHESES, COMPOSITIONS, AND METHODS TO TREAT CANCER

(75) Inventors: Barbara S. Beckman, New Orleans, LA (US); Maryam Foroozesh, Metairie, LA (US); Jiawang Liu, Metairie, LA (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 268 days.

(21) Appl. No.: 13/148,857

(22) PCT Filed: Feb. 9, 2010

(86) PCT No.: PCT/US2010/023604
§ 371 (c)(1),
(2), (4) Date: Oct. 13, 2011

(87) PCT Pub. No.: WO2010/093615
PCT Pub. Date: Aug. 19, 2010

(65) Prior Publication Data
US 2012/0027844 A1 Feb. 2, 2012

Related U.S. Application Data

(60) Provisional application No. 61/275,764, filed on Sep. 2, 2009, provisional application No. 61/207,293, filed on Feb. 10, 2009.

(51) Int. Cl.
*C07C 233/05* (2006.01)
*A61K 31/65* (2006.01)
*A61K 31/165* (2006.01)
*C07C 233/65* (2006.01)

(52) U.S. Cl.
USPC ........... 564/152; 564/158; 564/159; 564/189; 564/224; 564/272; 564/275; 564/355; 564/360; 514/613; 514/616; 514/620; 514/629; 514/641; 514/655

(58) Field of Classification Search
USPC ......... 564/152, 158, 159, 189, 224, 272, 275, 564/355, 360; 514/613, 616, 620, 629, 641, 514/655
See application file for complete search history.

(56) References Cited

U.S. PATENT DOCUMENTS 7,629,385 B2 * 12/2009 Braxmeier et al. ........... 514/579

FOREIGN PATENT DOCUMENTS

| WO | 01/38295 A1 | 5/2001 |
| WO | 01/72701 A1 | 10/2001 |

OTHER PUBLICATIONS

Ghering et al, J. of Lipid Research, 2006, 47(12), 2781-2788.*
Bielawaka et al, Journal of Biological Chemistry, 1993, 268(35), 26226-32.*
Carter et al., Chemotherapy of Cancer, second edition, John Wiley & Sons, N.Y., N.Y., 1981, pp. 362-365.*
PCT/US2010/023604, International Search Report and Written Opinion dated Sep. 30, 2010, 13 pp.
Antoon et al., "Design, synthesis, and biological activity of a family of novel ceramide analogues in chemoresistant breast cancer cells" Journal of Medicinal Chemistry, vol. 52, No. 18, pp. 5748-5752 and Supporting Information pp. S1-S5 (Sep. 24, 2009; published on web Aug. 20, 2009).
Antoon et al., "Novel d-erythro N-octanoyl sphingosine analogs as chemo- and endocrine-resistant breast cancer therapeutics" Cancer Chemotherapy and Pharmacology, vol. 65, No. 6, pp. 1191-1195 (2010).
Boddapati et al., "Mitochondriotropic liposomes" Journal of Liposome Research, vol. 15, pp. 49-58 (2005).
Boddapati et al., "Organelle-targeted nanocarriers: Specific delivery of liposomal ceramide to mitochondria enhances its cytotoxicity in vitro and in vivo" NanoLetters, vol. 8, No. 8, pp. 2559-2563 (2008).
Chang et al., "The synthesis and biological characterization of a ceramide library" Journal of the American Chemical Society, vol. 124, No. 9, pp. 1856-1857 (2002).
Chung et al., "Stereoselective synthesis of beta-amino alcohols: Practical preparation of all four stereomers of N-PMB-protected sphingosine from L- and D-serine" Tetrahedron: Asymmetry, vol. 10, No. 8, pp. 1441-1444 (1999).
Disadee et al., "Chirality transfer from guanidinium ylides to 3-alkenyl (or 3-alkynyl) aziridine-2-carboxylates and application to the syntheses of (2R,3S)-3-hydroxyleucinate and D-erythro-sphingosine" Journal of Organic Chemistry, vol. 70, No. 23, pp. 9399-9406 (2005).
Granot et al., "Caspase-dependent and -independent cell death of Jurkat human leukemia cells induced by novel synthetic ceramide analogs" Leukemia, vol. 20, pp. 392-399 (2006).
Gududuru et al., "Synthesis and biological evaluation of novel cytotoxic phospholipids for prostate cancer" Bioorganic & Medicinal Chemistry Letters, vol. 14, pp. 4919-4923 (2004).
Senkal et al, "Potent antitumor activity of a novel cationic pyridinium-ceramide alone or in combination with gemcitabine against human head and neck squamous cell carcinomas in vitro and in vivo" The Journal of Pharmacology and Experimental Therapeutics, vol. 317, No. 3, pp. 1188-1199 (2006).

(Continued)

*Primary Examiner* — Shailendra Kumar
(74) *Attorney, Agent, or Firm* — Calfee, Halter & Griswold LLP; Harry J. Guttman

(57) ABSTRACT

Compounds and their syntheses are disclosed herein. Compositions and pharmaceutical compositions comprising a compound are also described, and include compositions also comprising liposomes. Methods for the treatment of cancer in animals comprising administering a compound or a composition comprising a compound are also described.

34 Claims, 28 Drawing Sheets

(56) References Cited

OTHER PUBLICATIONS

Struckhoff et al., "Novel ceramide analogs as potential chemotherapeutic agents in breast cancer" The Journal of Pharmacology and Experimental Therapeutics, vol. 309, No. 2, pp. 523-532 (2004).

Suzuki et al., "Biochemical studies on carbohydrates. CLXXVIII. On molecular aggregation in solution of a group-active mucopolysaccharide from pig stomach mucus" The Tohoku Journal of Experimental Medicine, vol. 62, No. 1, pp. 19-26 (1955).

Weiss, "Synthesis of several oxazolidines and cycloacetals of sphingosine and dihydrosphingosine. IV" Journal of Organic Chemistry, vol. 26, pp. 491-497 (1961).

Yoshiizumi et al., "Studies on scavenger receptor inhibitors. Part 1: Synthesis and structure—activity relationships of novel derivatives of sulfatides" Bioorganic & Medicinal Chemistry, vol. 10, No. 8, pp. 2445-2460 (2002).

Zehavi, "Synthesis of potentially caged sphingolipids, possible precursors of cellular modulators and second messengers" Chemistry and Physics of Lipids, vol. 90, Nos. 1-2, pp. 55-61 (1997).

* cited by examiner

[Compound II-1] (μM)

[Compound II-4] (μM)

COMPOUNDS, THEIR SYNTHESES, COMPOSITIONS, AND METHODS TO TREAT CANCER

CROSS-REFERENCE TO RELATED APPLICATIONS

This application is a National Stage Entry of International Application No. PCT/US2010/023604 filed Feb. 9, 2010, which is incorporated by reference in its entirety, which claims the benefit of U.S. Provisional Application No. 61/207,293, filed Feb. 10, 2009, which is herein incorporated by reference in its entirety, and which also claims the benefit of U.S. Provisional Application No. 61/275,764, filed Sep. 2, 2009, which is herein incorporated by reference in its entirety.

GOVERNMENT RIGHTS

This invention was made in part with government support under NIH Grant Number 5G12RR026260-03 awarded by the National Institutes of Health from the National Center for Research Resources. The U.S. Government may have certain rights in the invention.

BACKGROUND

Some aspects of the invention relate to compounds, their methods of syntheses, their compositions, and their uses to treat cancer, including but not limited to, breast cancer, kidney cancer, colon cancer, rectal cancer, ovarian cancer, stomach cancer, uterine cancer, carcinoma in situ, and leukemia.

Some research may suggest that pathogenic alterations in endogenous ceramide levels contribute to cancer (e.g., breast cancer) chemoresistance. The bioactive sphingolipid ceramide may be a therapeutic target because it can be involved in the regulation of cellular apoptosis and survival. Several chemotherapeutic agents, including paclitaxol and doxorubicin, can induce apoptosis through induction of ceramide signaling. In fact, decreased synthesis and increased metabolism of the apoptotic sphingolipid ceramide can be a mechanism of chemoresistance in human breast cancer.

Treatment options for cancer can include one or more of surgical intervention, chemotherapy, radiation therapy, and adjuvant systematic therapies. Adjuvants may include but are not limited to chemotherapy, radiation therapy, and endocrine therapies, such as administration of LHRH agonists; antiestrogens, such as tamoxifen; high-dose progestogens; aromatase inhibitors; and/or adrenalectomy.

In recent years, the development of targeted molecular therapeutics has become increasingly based upon the identification of the precise molecular abnormalities that are responsible for malignant progression in human cancers. The identification and molecular characterization of signaling pathways responsible for abnormal growth, inhibition of apoptosis, cellular invasion and metastasis, and angiogenesis have generated some targets for new anticancer drugs. Therapy with tamoxifen and aromatase inhibitors has been a successful targeted therapy for decades. Anthracyclines and taxanes can be (individually or together) part of chemotherapy.

The monoclonal antibody trastuzumab is one example of a targeted therapy for breast cancer. Trastuzumab can be used to treat breast cancers that overproduce a protein called human epidermal growth factor receptor 2 or HER2. This protein is overproduced in about 20% of breast cancers. These HER2-overproducing cancers tend to be more aggressive and are more likely to recur. Trastuzumab targets the HER2 protein, and this antibody, in conjunction with adjuvant chemotherapy, can lower the risk of HER2-overproducing breast cancer recurrence by 50% compared to chemotherapy alone. Clinical trials have demonstrated trastuzumab as an important component of some first-line treatments. In particular, the combination with taxanes and vinorelbine has been established. The addition of trastuzumab to chemotherapy can improve disease-free and overall survival.

Chemotherapy can be used as a single-agent or as a combination, possibly with new targeted therapies where relevant. Resistance to chemotherapeutic agents can be an obstacle to successful management of patients with cancer. Some agents become increasingly ineffective in progressive disease and tumors are then deemed to be drug resistant.

While certain features of this invention shown and described below are pointed out in the claims, the invention is not intended to be limited to the details specified, since a person of ordinary skill in the relevant art will understand that various omissions, modifications, substitutions and changes in the forms and details of the invention illustrated and in its operation may be made without departing in any way from the spirit of the present invention. No feature of the invention is critical or essential unless it is expressly stated as being "critical" or "essential."

SUMMARY

According to some embodiments of the present invention, compounds for Formula (I) and Formula (II), as described herein, are provided. In some instances, the $IC_{50}$ of a compound against a cancer cell determined by a clonogenic survival assay is not greater than about 20 µM.

In accordance with other embodiments of the present invention, a composition comprising a compound is described. The composition may be a pharmaceutical composition and in some instances also comprises a liposome.

In accordance with another set of embodiments of the present invention, syntheses of the compounds are provided and, in some instances, include condensation of certain starting materials or intermediates with aldehydes or carboxylic acids.

In accordance with other embodiments of the invention, methods for treating cancer by administering a compound to an animal (such as a human) are described. In some instances, the cancer is breast cancer. In exemplary embodiments, the compound interferes with ceramidase in the one or more cancer cells.

Other embodiments of the present invention will be apparent in light of the description of the invention provided herein.

BRIEF DESCRIPTION OF THE DRAWINGS

The following drawings form part of the present specification and are included to further demonstrate certain aspects of the present invention. The invention may be better understood by reference to one or more of these drawings in combination with the description of specific embodiments presented herein.

DETAILED DESCRIPTION

Figure 1:
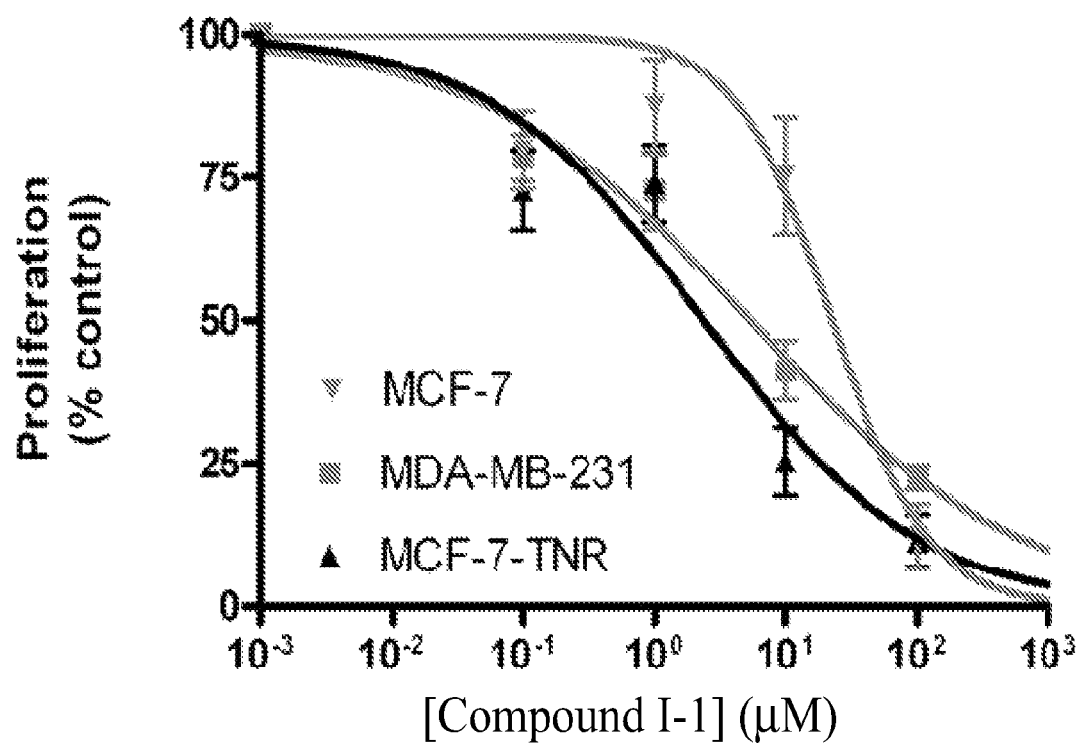
FIG. 1 demonstrates the inhibitory effect of compound I-1 on breast cancer cell lines MCF-7, endocrine resistant MDA-MB-231, and chemoresistant MCF-7-TNR.
Figure 2:
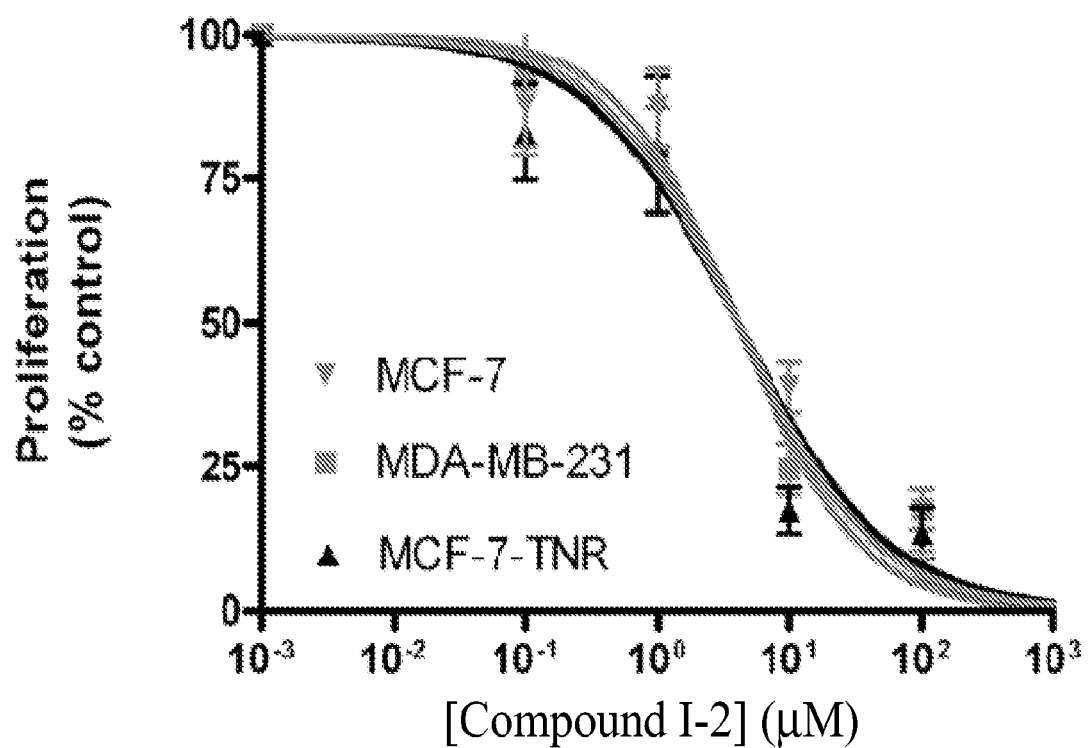
FIG. 2 demonstrates the inhibitory effect of compound I-2 on breast cancer cell lines MCF-7, endocrine resistant MDA-MB-231, and chemoresistant MCF-7-TNR.
Figure 3:
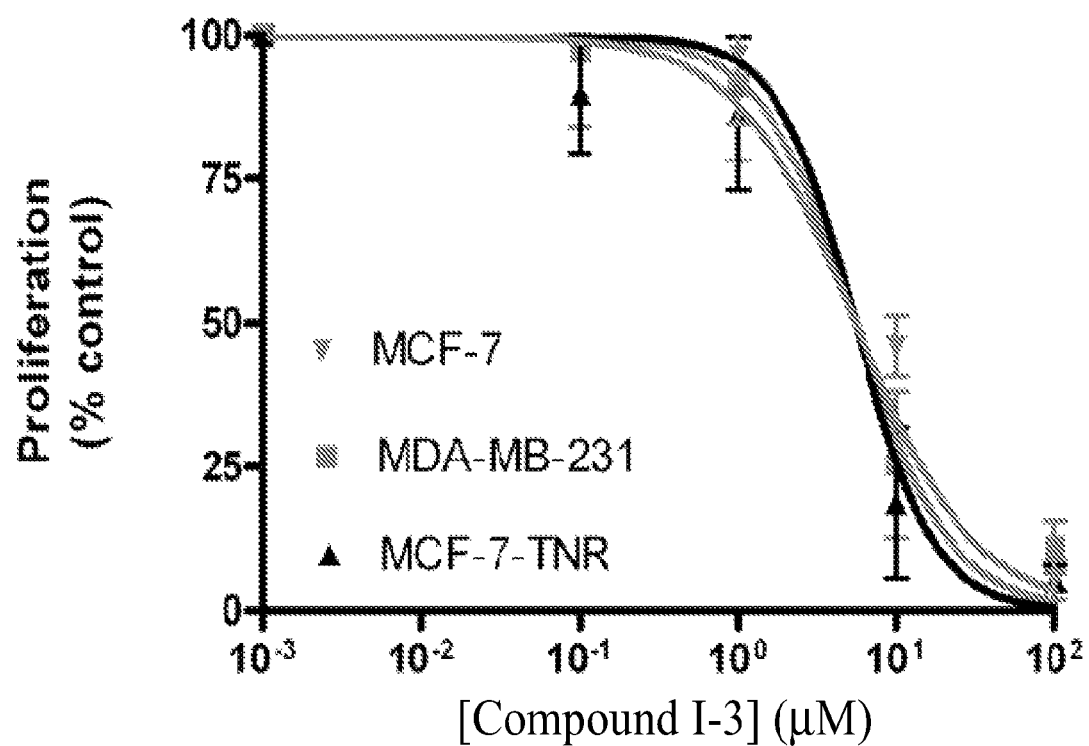
FIG. 3 demonstrates the inhibitory effect of compound I-3 on breast cancer cell lines MCF-7, endocrine resistant MDA-MB-231, and chemoresistant MCF-7-TNR.
Figure 4:
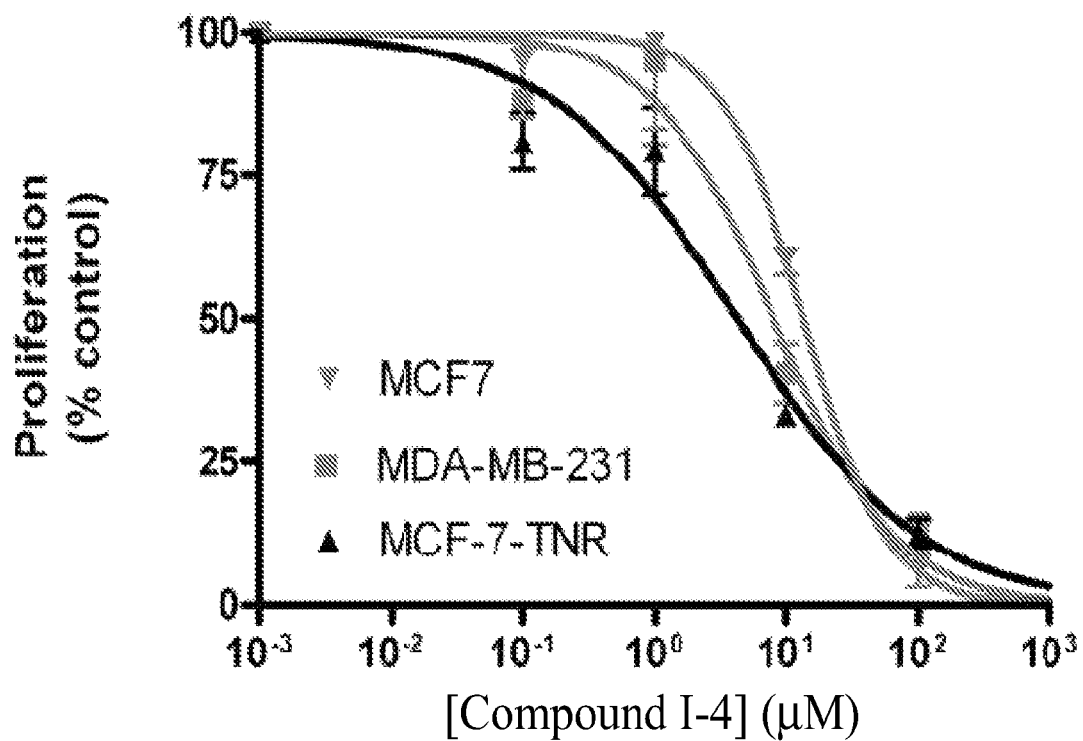
FIG. 4 demonstrates the inhibitory effect compound I-4 on breast cancer cell lines MCF-7, endocrine resistant MDA-MB-231, and chemoresistant MCF-7-TNR

Some embodiments of the invention include compounds chosen from:

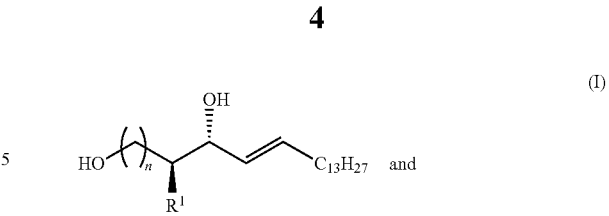

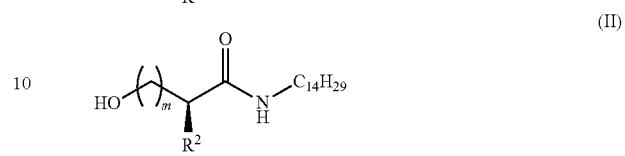

$R^1$ can be selected from:

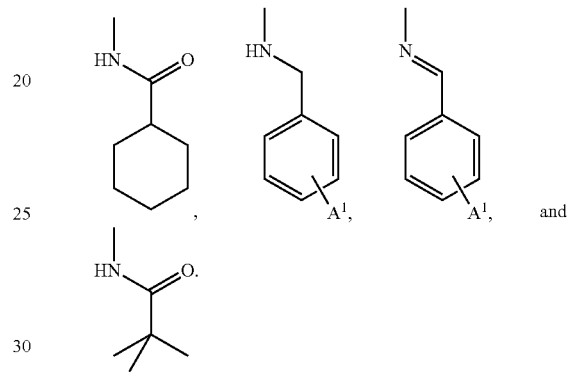

n can be 1, 2, or 3. The moiety $A^1$ can be at the 2-, 3-, or 4-position of the ring, and can be —H, —NO$_2$, —CH$_3$, —CH$_2$CH$_3$, —CH$_2$CH$_2$CH$_3$, —CHCH$_3$CH$_3$, —Cl, —Br, —I, —OCH$_3$, —OCH$_2$CH$_3$, —CN, acyl groups, or —OH.

$R^2$ can be selected from:

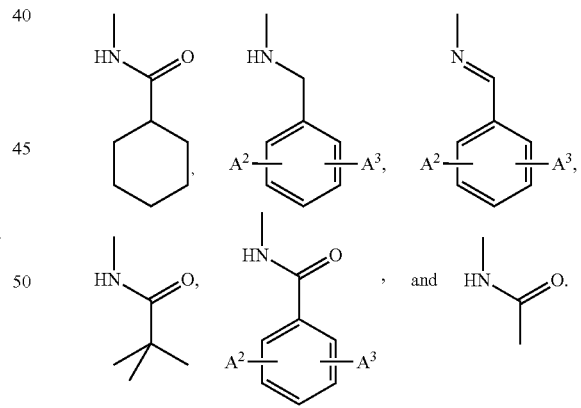

m can be 1, 2, or 3. $A^2$ and $A^3$ can be the same or different, can be at the 2-, 3-, 4-, 5-, or 6-position of the ring, and can be selected from —H, —NO$_2$, —CH$_3$, —CH$_2$CH$_3$, —CH$_2$CH$_2$CH$_3$, —CHCH$_3$CH$_3$, —Cl, —Br, —I, —OCH$_3$, —OCH$_2$CH$_3$, —CN, acyl groups, or —OH. In some embodiments, $A^2$ is in the 2-position and $A^3$ is in the 6-position. In still other embodiments, $A^2$ is in the 2-position and $A^3$ is in the 6-position, and $A^2$ and $A^3$ are chosen from electron withdrawing groups including but not limited to —NO$_2$, —Cl, —Br, —I, —OCH$_3$, —OCH$_2$CH$_3$, —CN, acyl groups, or —OH. In other embodiments, $A^2$ and $A^3$ are not in the 3- or 5-position.

An acyl group can be chosen from, but is not limited to, —C(O)CH₃, —C(O)CH₂CH₃, —C(O)(CH₂)₂CH₃, and —C(O)(CH₂)₃CH₃.
In some exemplary embodiments, the compound is chosen from:
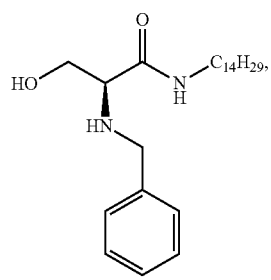
Compound I-1
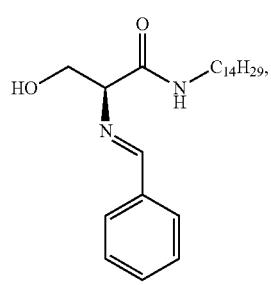
Compound I-2
Compound I-3
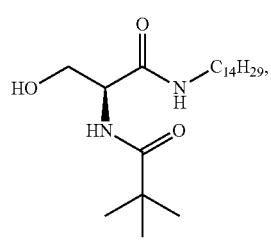
Compound I-4
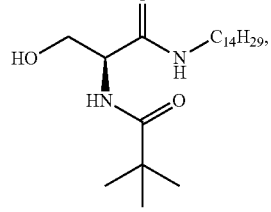
Compound II-1
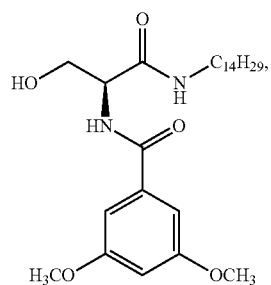
-continued
Compound II-2
Compound II-3
Compound II-4
Compound II-5
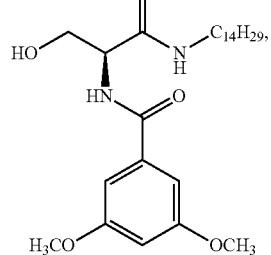
Compound II-6
Compound II-7
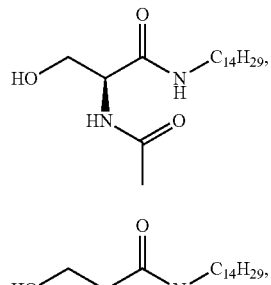
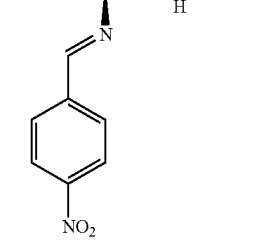
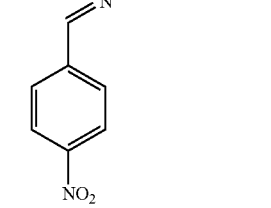

Compound II-8
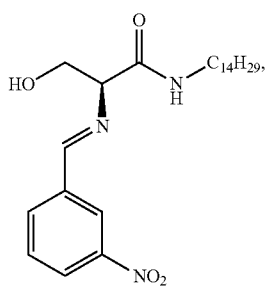
Compound II-9
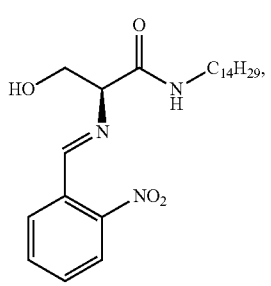
Compound II-10
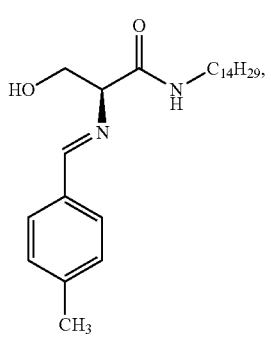
Compound II-11
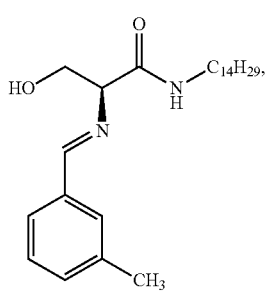
Compound II-12
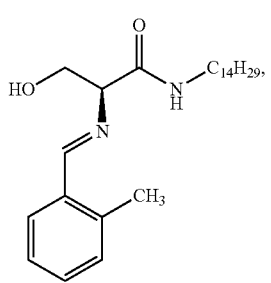
Compound II-13
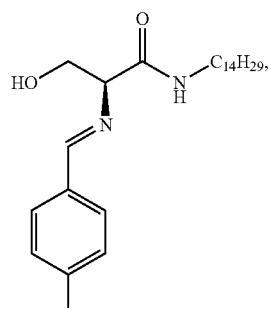
Compound II-14
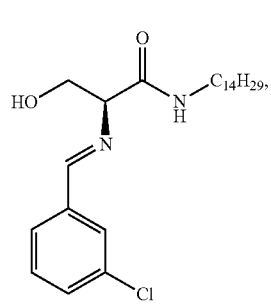
Compound II-15
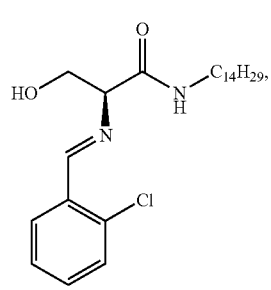
Compound II-16
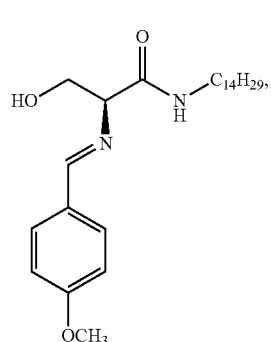
Compound II-17
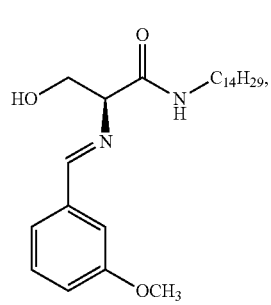

-continued

Compound II-18
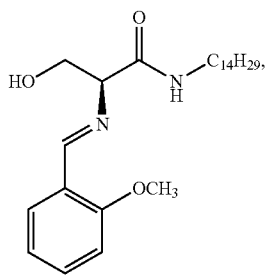

Compound II-19
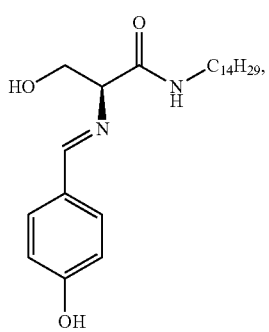

Compound II-20
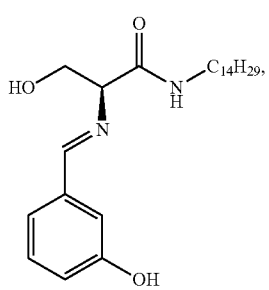

Compound II-21
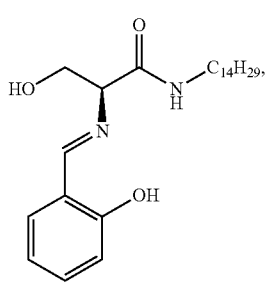

Compound II-22
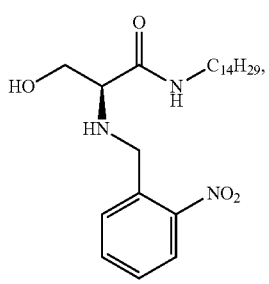

Compound II-23
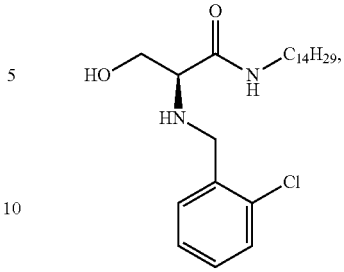

Compound II-24
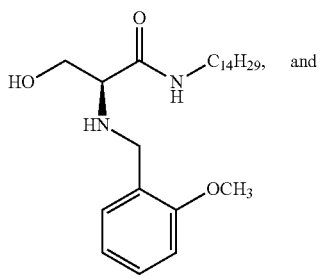

and

Compound II-25
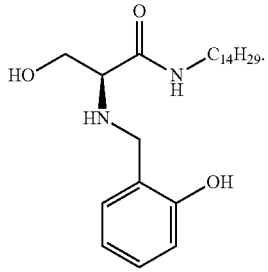

Some embodiments of the invention include compounds of Formula (I) or Formula (II) in the form of free bases, salts, optical isomers, geometric isomers, salts of isomers, and derivatives. Such salts include uncharged molecules, components of molecular complexes, or non-irritating pharmacologically acceptable salts, e.g. the hydrochloride, hydrobromide, sulfate, phosphate, nitrate, borate, acetate, maleate, tartrate, salicylate, etc. For acidic compounds, salts include metals, amines, or organic cations (e.g. quaternary ammonium salts). Furthermore, derivatives of the compounds (such as ethers, esters, amides, etc.) include those which have desirable retention and release characteristics but which are easily hydrolyzed by body pH, enzymes, etc.

In some embodiments, the compounds incorporate an amide functional group in the long carbon chain. The presence of this amide functional group can, in some instances, modify polarity. The carbon chain length can be kept approximately the same as the known ceramides in order to keep the optimum lipid solubility and facility of passage through membranes. Other structural variations include, but are not limited to, the presence and absence of the original carbonyl group and different sizes and shapes of the substituents on the original nitrogen. In some instances, ceramide can be modified to prevent degradation into sphingosine by modifying the amide group where the ceramidase-catalyzed hydrolysis reaction can occur; for example, the presence of an imine group, as exemplified in compounds I-3, II-3, and II-7 to II-21, appears to reduce or prevent hydrolysis by ceramidase.

Some compounds of Formula (I) and (II) can inhibit growth of MCF-7, MDA-MB-231, and MCF7-TN-R human breast cancer cells in an in vitro model as exemplified by MTT viability assays and clonogenic survival assays. More generally, some compounds of Formula (I) and (II) can interfere with ceramidase, for example, by blocking sphingosine production or preventing ceramide analog depletion.

The $IC_{50}$ for some compounds used in the MTT viability assay with MCF-7, MDA-MB-231, or MCF7-TN-R human breast cancer cells can be not greater than about 0.1 µM, not greater than about 0.5 µM, not greater than about 1.0 µM, not greater than about 5.0 µM, not greater than about 10 µM, not greater than about 20 µM, at least about 0.001 µM, at least about 0.01 µM, at least about 0.1 µM, or at least about 1.0 µM.

The $IC_{50}$ for some compounds used in the clonogenic survival assay with MCF-7, MDA-MB-231, or MCF7-TN-R human breast cancer cells can be not greater than about 0.1 µM, not greater than about 0.5 µM, not greater than about 1.0 µM, not greater than about 5.0 µM, not greater than about 10 µM, not greater than about 20 µM, at least about 0.001 µM, at least about 0.01 µM, at least about 0.1 µM, or at least about 1.0 µM.

For some compounds the selectivity to inhibit cell growth of cancer cells compared to normal breast epithelial cells can be determined by the ratio of $IC_{50}$ from proliferation assays of normal cells (e.g, MCF10A) to the cancer cells (e.g., MCF-7, MDA-MB-231, or MCF7-TN-R). This ratio (i.e., $IC_{50}$ of normal cells divided by $IC_{50}$ of cancel cells) can be at least about 25, at least about 50, at least about 100, at least about 200, at least about 500, not greater than 250, not greater than 750, or not greater than 1000.

Some embodiments of this invention include the syntheses of compounds. Syntheses can include condensation of one or more starting compounds (or intermediates) with, for example, aldehydes or carboxylic acids. In some instances, the short chain ceramide D-erythro N-octanoyl sphingosine, also known as C8-ceramide, can be used to synthesize some of compounds. Other starting compounds (or intermediates) can include

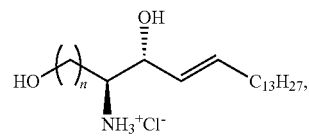

such as sphingosine, and

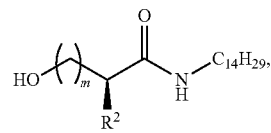

such as (S)-2-amino-3-hydroxy-N-tetradecylpropanamide. Here, n and m can be the same or different and can be 1, 2, or 3.

In some embodiments, syntheses of the compounds can include two or more strategies to modify the ceramide structure. In one strategy, cycloalkyl groups or branched alkyl groups can be introduced as substituents on the amide group; this can, in some instances, replace the flexible heptyl chain to enhance the rigidity and steric hindrance and shield this hydrolysis site. In another strategy, the amide functional group can be replaced with an amine functional group or an imine functional group; in some cases, this can prevent amide hydrolysis by the enzyme ceramidase.

In some syntheses, after condensation, reduction can be used to, for example, saturate one or more double bonds. This reduction can occur, in some instances, using $NaBH_3CN$.

In some embodiments, compounds can be synthesized according to Scheme A, which exemplifies the synthesis of I-1 to I-4.

Scheme A

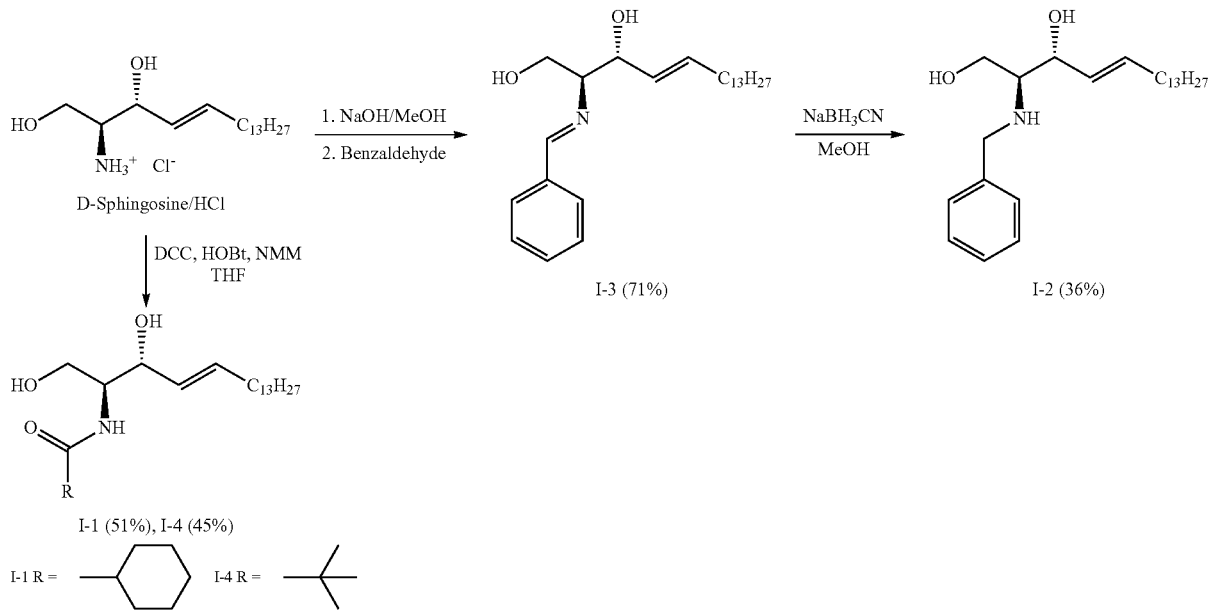

In some embodiments, the compounds can be synthesized according to the Scheme B, which exemplifies the synthesis of II-1 to II-4.

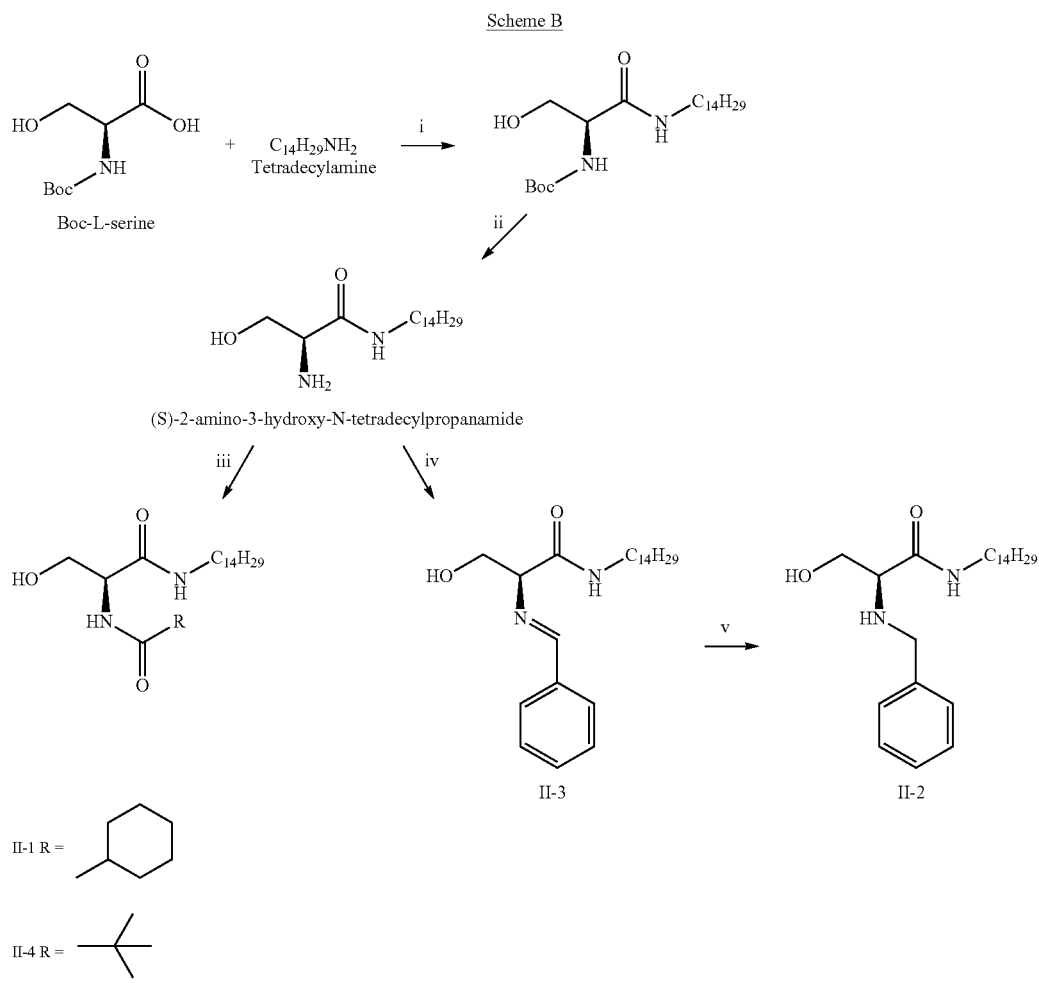

In scheme B, the following reaction conditions can be used: i) DCC/HOST in THF 0° C.; ii) TFA/CH$_2$Cl$_2$ (0° C.), and NaCO$_3$/Ethyl acetate; iii) DCC/HOBT in THF 0° C., and cyclohexanecarboxylic acid (for compound II-1) or pivalic acid (for compound II-4); iv) NaOH/benzaldehyde in methanol; v) NaBH$_3$CN/methanol.

The compounds of Formula (I) and Formula (II) can be administered to animals by any number of administration routes or formulations. The compounds can also be used to treat animals for a variety of diseases. Animals include but are not limited to canine, bovine, porcine, avian, mammalian, and human.

Diseases that can be treated using the compounds include, but are not limited to cancers, such as cancerous tumors. Cancers that can be treated include breast cancer, kidney cancer, colon cancer, rectal cancer, ovarian cancer, stomach cancer, uterine cancer, carcinoma in situ, and leukemia. Other cancers that can be treated include cancers that interfere with ceramidase, for example, by blocking sphingosine production or preventing ceramide analog depletion. In some embodiments, the compounds of Formula (I) and (II) can be useful therapy against chemosensitive cancers or chemoresistant cancers, including breast cancer.

As used herein, the term "breast cancer" refers to any cancer having its origin in breast cells, and includes metastatic and local forms of breast cancer. The term "minimize" or "reduce," or a derivative thereof, includes a complete or partial inhibition of a specified biological effect (which is apparent from the context in which the term minimize is used).

Treatment can also include one or more of surgical intervention, chemotherapy, radiation therapy, and adjuvant systematic therapies. Adjuvants may include but are not limited to chemotherapy, radiation therapy, and endocrine therapies, such as administration of LHRH agonists; antiestrogens, such as tamoxifen; high-dose progestogens; aromatase inhibitors; and/or adrenalectomy. Chemotherapy can be used as a single-agent or as a combination with known or new therapies.

The route of administration of the compounds may be of any suitable route such as that which provides a concentration in the blood corresponding to a therapeutic concentration. Administration routes that can be used, but are not limited to the oral route, the parenteral route, the cutaneous route, the nasal route, the rectal route, the vaginal route and the ocular route. The choice of administration route can depend on the compound identity, such as the physical and chemical properties of the compound, as well as the age and weight of the animal, the particular disease and the severity of the disease. Of course, combinations of administration routes can be administered, as desired.

One or more compounds of Formula (I) and Formula (II) can be part of a composition and can be in an amount from about 1% to about 95% by weight of the total composition (or from about 10% to about 90%, or from about 25% to about 75%).

One or more compounds of Formula (I) and Formula (II) can also be part of a liposome delivery system such as those described in Boddapati et al., Nano Lett., Vol. 8, No. 8, pp. 2559-2563 (2008) and Boddapati et al., J. Liposome Research, Vol. 15, pp. 49-58 (2005). In some instances, the liposome delivery system can include nanocarriers which can be modified to improve the efficiency or provide targeting (e.g., to specific organs or subcellular structures, such as mitochondria) of drug delivery. Such modifications include but are not limited to conjugation of triphenylphosphonium to lipids (such as a stearyl portion of a lipid or other portions of phospholipids) which are then incorporated into lipid bilayers.

One or more compounds of Formula (I) and Formula (II) can be part of a pharmaceutical composition and can be in an amount from about 1% to about 95% by weight of the total composition (or from about 10% to about 90%, or from about 25% to about 75%). The composition can be presented in a dosage form which is suitable for the oral, parenteral, rectal, cutaneous, nasal, vaginal, or ocular administration route. The composition can be of the form of, for example, tablets, capsules, pills, powders granulates, suspensions, emulsions, solutions, gels (including hydrogels), pastes, ointments, creams, plasters, drenches, delivery devices, suppositories, enemas, injectables, implants, sprays, aerosols or other suitable forms.

Pharmaceutical compositions can be formulated to release the active compound substantially immediately upon the administration or any substantially predetermined time or time after administration. Such formulations can include, for example, controlled release formulations such as various controlled release compositions and coatings.

Other formulations include those incorporating the drug (or control release formulation) into food, food stuffs, feed, or drink.

EXAMPLES

All synthesis chemicals and solvents were purchased from Sigma-Aldrich Company except D-sphingosine/HCl which was purchased from CNH Technologies Inc. All coupling reactions were carried out under anhydrous conditions. The purities of the intermediates and the products were confirmed by HPLC (hp HEWLETT PACKARD SERIES 1050, phenomenex Gemini-NX 5u Cl 8 110A) and thin layer chromatography (Whatman 250 μm) LAYER, $UV_{254}$, Flexible plates for TLC and SILICA GEL IB2-F). Chromatography was performed on HPTLC Silica gel 60 $F_{254}$. $^1$H NMR and $^{13}$C NMR spectra were obtained on a Varian 300 MHz NMR spectrometer. Mass spectral data was determined using an Agilent 6890N Network GC System with 5975C inert MSD. Elemental analysis was performed by Atlantic Microlab Inc.

N-((2S,3R,E)-1,3-dihydroxyoctadec-4-en-2-yl)cyclohexanecarboxamide (Compound I-1) was synthesized by adding 40 mg (0.29 mmol) of tert-butyl alcohol (HOBt) and 100 mg (0.29 mmol) of D-sphingosine/HCl at 0° C. to the solution of 38 mg (0.29 mmol) of cyclohexanecarboxylic acid in 25 mL of anhydrous tetrahydrofuran (THF). After 5 min, 67 mg (0.33 mmol) of dicyclohexylcarbodiimide (DCC) was added, and the pH of the solution was adjusted to 8 with 4-methylmorpholine. The reaction mixture was stirred at 0° C. for 2 h and at room temperature overnight. On evaporation the residue was dissolved in 100 mL of ethyl acetate. The solution was washed successively with saturated sodium bicarbonate, 5% potassium bisulfate, and saturated sodium chloride, and the organic phase was separated and dried over anhydrous magnesium sulfate for 2 h. After filtration and evaporation under reduced pressure, the crude product was recrystallized in ethyl ether to obtain 60 mg (51%) of N-((2S,3R,E)-1,3-dihydroxyoctadec-4-en-2-yl)cyclohexanecarboxamide as colorless powder. GC/MS (m/e): 391 $[M+H_2O]^+$. $^1$H NMR ($d_6$-DMSO, 300 MHz) δ/ppm=7.224 (d, J=8.4 Hz, 1H), 5.513 (dt, J=15.3 Hz, J=6.6 Hz, 1H), 5.345 (dd, J=15.3 Hz, J=6.6 Hz, 1H), 4.789 (d, J=5.1 Hz, 1H), 4.422 (t, J=5.4 Hz, 1H), 3.872 (q, J=6.0 Hz, 1H), 3.636 (m, 1H), 3.446 (m, 2H), 2.088 (m, 1H), 1.917 (m, 2H), 1.652 (m, 6H), 1.225-1.157 (m, 26H), 0.843 (t, J=6.6 Hz, 3H). $^{13}$C NMR ($d_6$-DMSO, 75 MHz) δ/ppm=132.083, 131.506, 72.063, 61.298, 55.665, 44.657, 32.358, 31.979, 30.172, 29.732, 29.656, 29.382, 29.246, 26.194, 26.042, 22.778, 14.624. Anal. Calcd for $C_{25}H_{47}NO_3$: C, 73.30; H, 11.56; N, 3.42; O, 11.72. Found: C, 72.99; H, 11.64; N, 3.74; O, 11.91.

To synthesize (2S,3R,E)-2-(benzylamino)octadec-4-ene-1,3-diol (Compound I-2), 20 mg (0.32 mmol) of sodium cyanoborohydride ($NaBH_3CN$) was added to the solution of 80 mg (0.21 mmol) (2S,3R,E)-2-((E)-benzylideneamino)octadec-4-ene-1,3-diol in 10 mL of methanol. The reaction mixture was stirred at room temperature for 10 h, and evaporated under vacuum. The residue was purified by thin layer chromatography to give 30 mg (36%) of (2S,3R,E)-2-(benzylamino)octadec-4-ene-1,3-diol as colorless powder. GC/MS (m/e): 388 $[M+H]^+$, 372 $[M+.OH]^+$, 358 $[M-[.CH_2=OH]]^+$. $^1$H NMR ($d_6$-DMSO, 300 MHz) δ/ppm=7.323~7.193 (m, 5H), 5.507 (m, 2H), 4.602 (d, J=3.6 Hz, 1H), 4.311 (br, 1H), 4.004 (m, 1H), 3.750 (s, 2H), 3.400 (m, 1H), 3.292 (m, 1H), 2.459 (m, 1H), 1.962 (m, 2H), 1.218 (m, 22H), 0.840 (t, J=6.6 Hz, 3H). $^{13}$C NMR ($d_6$-DMSO, 75 MHz) δ/ppm=132.113, 131.126, 128.727, 128.591, 127.163, 71.881, 63.894, 61.116, 51.960, 32.419, 31.964, 29.717, 29.382, 29.200, 22.778, 14.624. Anal. Calcd for $C_{25}H_{43}NO_2$: C, 77.07; H, 11.12; N, 3.60; O, 8.21. Found: C, 75.79; H, 11.26; N, 3.55; O, 8.20.

To synthesize (2S,3R,E)-2-((E)-benzylideneamino)octadec-4-ene-1,3-diol (Compound I-3), a solution of 100 mg (0.29 mmol) of D-sphingosine/HCl, 11.6 mg (0.29 mmol) of sodium hydroxide (NaOH), 0.05 mL of benzaldehyde in 10 mL of methanol was stirred at room temperature. After 1 hour, the solution was evaporated under reduced pressure, and the residue was washed with cooled methanol to yield 80 mg (71%) of (2S,3R,E)-2-((E)-benzylideneamino)octadec-4-ene-1,3-diol as colorless powder. GC/MS (m/e): 387 $M^+$, 370 $[M+.OH]^+$, 356 $[M+[.CH_2=OH]]^+$. $^1$H NMR ($d_6$-DMSO, 300 MHz) δ/ppm=8.189 (s, 1H), 7.709 (t, J=3.6 Hz, 2H), 7.409 (m, 3H), 5.431 (m, 2H), 4.781 (d, J=4.2 Hz, 1H), 4.431 (br, 1H), 4.059 (m, 1H), 3.759 (m, 1H), 3.408 (m, 1H), 3.162 (m, 1H), 1.907 (m, 2H), 1.221~1.119 (m, 22H), 0.838 (t, J=6.6 Hz, 3H). $^{13}$C NMR ($d_6$-DMSO, 75 MHz) δ/ppm=161.523, 137.063, 132.341, 131.354, 130.959, 129.092, 128.621, 78.501, 72.792, 63.105, 32.358, 31.994, 29.747, 29.717, 29.625, 29.565, 29.474, 29.413, 29.033, 22.793, 14.624. Anal. Calcd for $C_{25}H_{41}NO_2$: C, 77.47; H, 10.66; N, 3.61; O, 8.26. Found: C, 76.84; H, 10.82; N, 3.75; O, 8.75.

To synthesize N-((2S,3R,E)-1,3-dihydroxyoctadec-4-en-2-yl)pivalamide (Compound I-4), 40 mg (0.29 mmol) of HOBt and 100 mg (0.29 mmol) of D-sphingosine/HCl were added at 0° C. to the solution of 30 mg (0.29 mmol) of pivalic acid in 25 mL of anhydrous THF. After 5 min, 67 mg (0.33 mmol) of DCC was added, and the pH of the solution was adjusted to 8 with 4-methylmorpholine. The reaction mixture was stirred at 0° C. for 2 h and at room temperature overnight. On evaporation the residue was dissolved in 100 ml of ethyl acetate. The solution was washed successively with saturated sodium bicarbonate, 5% potassium bisulfate, and saturated sodium chloride and the organic phase was separated and dried over anhydrous magnesium sulfate for 2 h. After filtration and evaporation under reduced pressure, the residue was purified by thin layer chromatography (chloroform/methanol 10/1) to obtain 0.50 g (45%) of N-((2S,3R,E)-1,3-dihydroxy-octadec-4-en-2-yl)pivalamide as colorless powder. GC/MS (m/e): 382 [M+H]$^+$, 366 [M+.OH]$^+$, 352 [M+[.CH$_2$=OH]]$^+$. $^1$H NMR (d$_6$-DMSO, 300 MHz) δ/ppm=6.708 (d, J=8.7 Hz, 1H), 5.513 (dt, J=15.3 Hz, J=6.3 Hz, 1H), 5.340 (dd, J=15.3 Hz, J=6.3 Hz, 1H), 4.819 (d, J=5.4 Hz, 1H), 4.444 (t, J=5.7 Hz, 1H), 3.926 (q, J=6.0 Hz, 1H), 3.643 (m, 1H), 3.493 (m, 2H), 1.916 (m, 2H), 1.224 (m, 22H), 1.052 (s, 9H), 0.843 (t, J=6.6 Hz, 3H). $^{13}$C NMR (d$_6$-DMSO, 75 MHz) δ/ppm=132.128, 131.445, 72.002, 61.237, 55.802, 32.328, 31.964, 29.717, 29.625, 29.382, 28.046, 22.778, 14.639. Anal. Calcd for C$_{23}$H$_{45}$NO$_3$: C, 72.01; H, 11.82; N, 3.65; O, 12.51. Found: C, 72.12; H, 11.65; N, 3.66; O, 12.80.

To synthesize (S)-tert-butyl 3-hydroxy-1-oxo-1-(tetradecylamino)propan-2-ylcarbamate (an intermediate), 1.32 g (9.76 mmol) of 1-hydroxybenzotriazole hydrate (HOBt) was added at 0° C. to the solution of 2.00 g (9.76 mmol) of N-Boc-L-serine in 60 ml of anhydrous tetrahydrofuran (THF dried over calcium chloride). The pH of the solution was adjusted to 8-9 with 4-methylmorpholine. After five minutes of stirring, 2.21 g (10.74 mmol) of N,N'-dicyclohexylcarbodiimide (DCC) was added. The solution of 2.08 g (9.76 mmol) of tetradecylamine in 3 mL of anhydrous THF was added to the solution of N-Boc-L-serine and the reaction mixture was stirred at 0° C. for two hours, and at room temperature overnight. On evaporation the residue was dissolved in 60 ml of ethyl acetate. The solution was washed successively with saturated sodium bicarbonate, 5% potassium bisulfate, and saturated sodium chloride and the organic phase was separated and dried over anhydrous magnesium sulfate for two hours. After filtration and evaporation under reduced pressure 3.57 g (91.5%) of (S)-tert-butyl 3-hydroxy-1-oxo-1-(tetradecylamino)propan-2-ylcarbamate was obtained as powder. $^1$H NMR (d$_6$-DMSO, 90 MHz) δ/ppm=7.708 (t, J=8.3 Hz, 1H), 6.507 (d, J=11.9 Hz, 1H), 4.765 (t, J=8.3 Hz, 1H), 3.881 (m, 1H), 3.525 (m, 2H), 3.076 (m, 2H), 1.401 (s, 9H), 1.589~0.740 (m, 36H). $^{13}$C NMR (d$_6$-DMSO, 75 MHz) δ/ppm=170.725, 155.784, 78.683, 62.558, 57.548, 39.161, 31.994, 29.732, 29.504, 29.413, 28.790, 26.953, 22.778, 14.548.

To synthesize (S)-2-amino-3-hydroxy-N-tetradecylpropanamide (an intermediate), at 0° C., to the solution of 1.00 g (2.50 mmol) of (S)-tert-butyl 3-hydroxy-1-oxo-1-(tetradecylamino)propan-2-ylcarbamate in 20 mL of dichloromethane (DCM), 3.0 mL of trifluoroacetic acid was added. After four hours of stirring, the solvent was removed under vacuum pressure, and the residue was crystallized in diethyl ether and petroleum ether to give 0.68 g (65.7%) of (S)-2-amino-3-hydroxy-N-tetradecylpropanamide as powder. $^1$H NMR (d$_6$-DMSO, 90 MHz) δ/ppm=8.358 (t, J=9.1 Hz, 1H), 8.112 (m, 3H), 4.583 (br, 1H), 3.715 (m, 3H), 3.093 (m, 2H), 1.531~0.677 (m, 27H). $^{13}$C NMR (d$_6$-DMSO, 75 MHz) δ/ppm=167.141, 61.040, 55.042, 39.449, 31.979, 29.747, 29.701, 29.489, 29.398, 26.968, 22.763, 14.563.

To synthesize (S)—N-(3-hydroxy-1-oxo-1-(tetradecylamino)propan-2-yl)cyclohexanecarboxamide (Compound II-1), at 0° C. to the solution of 0.16 g (1.20 mmol) of cyclohexanecarboxylic acid in THF (20 ml) and DMF (5 mL), 0.16 g (1.20 mmol) of HOBt and 0.50 g (1.20 mmol) of (S)-2-amino-3-hydroxy-N-tetradecylpropanamide were added. After five minutes, 0.30 g (1.45 mmol) of DCC was added, and the pH of the solution was adjusted to 8-9 with 4-methylmorpholine. The reaction mixture was stirred at 0° C. for two hours, and at room temperature overnight. On evaporation the residue was dissolved in 100 ml of ethyl acetate. The solution was washed successively with saturated sodium bicarbonate, 5% potassium bisulfate, and saturated sodium chloride and the organic phase was separated and dried over anhydrous magnesium sulfate for two hours. After filtration and evaporation under reduced pressure 0.40 g (81.3%) of (S)—N-(3-hydroxy-1-oxo-1-(tetradecylamino)propan-2-yl)cyclohexanecarboxamide was obtained as powder. ESI/MS (m/e) 411 [M+H]$^+$. $^1$H NMR (d$_6$-DMSO, 90 MHz) δ/ppm=7.559 (m, 2H), 4.762 (t, J=8.3 Hz, 1H), 4.195 (m, 1H), 3.495 (m, 3H), 3.020 (m, 2H), 1.912~0.711 (m, 37H). $^{13}$C NMR (d$_6$-DMSO, 75 MHz) δ/ppm=175.841, 170.649, 62.452, 55.604, 44.368, 39.145, 34.029, 31.979, 29.884, 29.717, 29.458, 29.382, 26.938, 26.164, 26.012, 25.146, 22.778, 14.609. Anal. Calcd for C$_{24}$H$_{46}$N$_2$O$_3$ C, 70.20; H, 11.29; N, 6.82; O, 11.69. Found: C, 69.34; H, 11.25; N, 6.52; O, 12.42.

To synthesize (S)-2-(benzylideneamino)-3-hydroxy-N-tetradecylpropanamide (Compound II-3), a mixture of 0.50 g (1.20 mmol) of (S)-2-amino-3-hydroxy-N-tetradecylpropanamide, 0.05 g (1.20 mmol) of NaOH, 0.13 g (1.20 mmol) of benzaldehyde, and 10 mL of methanol was stirred at room temperature for eight hours. The solvent was then evaporated under reduced pressure, and the residue was washed with cooled methanol to yield 0.32 g (68.7%) of (S)-2-(benzylideneamino)-3-hydroxy-N-tetradecylpropanamide as colorless powder. ESI/MS (m/e) 389 [M+H]$^+$. $^1$H NMR (d$_6$-DMSO, 90 MHz) δ/ppm=8.281 (s, 1H), 7.818 (m, 3H), 7.515 (m, 3H), 4.795 (br, 1H), 3.768 (m, 3H), 3.103 (m, 2H), 1.584~0.702 (m, 27H). $^{13}$C NMR (d$_6$-DMSO, 75 MHz) δ/ppm=170.497, 163.239, 136.532, 131.597, 129.198, 129.061, 76.254, 63.788, 39.039, 31.964, 29.808, 29.701, 29.382, 26.983, 22.763, 14.609. Anal. Calcd for C$_{24}$H$_{40}$N$_2$O$_2$ C, 74.18; H, 10.38; N, 7.21; O, 8.23. Found: C, 72.83; H, 10.44; N, 7.14; O, 8.77.

To synthesize (S)-2-(benzylamino)-3-hydroxy-N-tetradecylpropanamide (Compound II-2), to the solution of 0.20 g (0.52 mmol) of (S)-2-(benzylideneamino)-3-hydroxy-N-tetradecylpropanamide in 10 mL of methanol, 32 mg (0.52 mmol) of sodium borohydride (NaBH$_4$) was added. The reaction mixture was stirred at room temperature for ten hours before evaporation under vacuum. The residue was purified by thin layer chromatography to give 115 mg (57.5%) of (S)-2-(benzylamino)-3-hydroxy-N-tetradecylpropanamide as colorless powder. ESI/MS (m/e) 391 [M+H]$^+$. $^1$H NMR (d$_6$-DMSO, 90 MHz) δ/ppm=7.780 (t, J=8.3 Hz, 1H), 7.304 (m, 5H), 4.726 (br, 1H), 3.790~2.869 (m, 7H), 1.566~0.706 (m, 27H). $^{13}$C NMR (d$_6$-DMSO, 75 MHz) δ/ppm=172.425, 141.041, 128.788, 128.651, 127.361, 64.638, 63.150, 52.097, 38.902, 31.979, 29.853, 29.717, 29.413, 29.382, 27.014, 22.763, 14.609. Anal. Calcd for C$_{24}$H$_{42}$N$_2$O$_2$ C, 73.80; H, 10.84; N, 7.17; O, 8.19. Found: C, 71.64; H, 10.63; N, 6.75; O, 9.10.

To synthesize (S)-3-hydroxy-2-pivalamido-N-tetradecylpropanamide (Compound II-4), at 0° C. to the solution of 0.10 g (0.98 mmol) of trimethylacetic acid in THF (60 mL), 0.13 g (0.96 mmol) of HOBt and 0.40 g (0.97 mmol) of (S)-2-amino-3-hydroxy-N-tetradecylpropanamide were added. After five minutes, 0.23 g (1.12 mmol) of DCC was added, and the pH of the solution was adjusted to 8-9 with 4-methylmorpholine. The reaction mixture was stirred at 0° C. for two hours, and at room temperature overnight. On evaporation the residue was dissolved in 100 mL of ethyl acetate. The solution was washed successively with saturated sodium bicarbonate, 5% potassium bisulfate, and saturated sodium chloride and the organic phase was separated and dried over anhydrous magnesium sulfate for two hours. After filtration and evaporation under reduced pressure 0.28 g (72.9%) of (S)-3-hydroxy-2-pivalamido-N-tetradecylpropanamide was obtained as powder. ESI/MS (m/e) 385 [M+H]$^+$. $^1$H NMR (d$_6$-DMSO, 90 MHz) δ/ppm=7.642 (t, J=8.3 Hz, 1H), 7.088 (d, J=11.9 Hz, 1H), 4.818 (t, J=8.3 Hz, 1H), 4.198 (m, 1H), 3.552 (m, 2H), 3.037 (m, 2H), 1.124 (s, 9H), 1.572-0.728 (m, 36H). $^{13}$C NMR (d$_6$-DMSO, 75 MHz) δ/ppm=177.861, 170.558, 62.406, 55.908, 39.161, 31.979, 29.732, 29.701, 29.443, 29.398, 27.910, 26.938, 22.778, 14.609. Anal. Calcd for C$_{22}$H$_{44}$N$_2$O$_3$ C, 68.70; H, 11.53; N, 7.28; O, 12.48.

To synthesize (S)—N-(3-hydroxy-1-oxo-1-(tetradecylamino)propan-2-yl)-3,5-dimethoxybenzamide (Compound II-5), at 0° C. to the solution of 0.10 g (0.55 mmol) of 3,5-dimethoxybenzoic acid in THF (80 mL), 0.08 g (0.59 mmol) of HOBt and 0.23 g (0.55 mmol) of (S)-2-amino-3-hydroxy-N-tetradecylpropanamide were added. Then 0.12 g (0.60 mmol) of DCC was added, and the pH of the solution was adjusted to 8 with 4-methylmorpholine. The reaction mixture was stirred at 0° C. for two hours, and at room temperature overnight. On evaporation the residue was dissolved in 130 mL of ethyl acetate. The solution was washed successively with saturated sodium bicarbonate, 5% potassium bisulfate, and saturated sodium chloride and the organic phase was separated and dried over anhydrous magnesium sulfate for two hours. After filtration and evaporation under reduced pressure, 0.05 g (20.0%) of (S)—N-(3-hydroxy-1-oxo-1-(tetradecylamino)propan-2-yl)-3,5-dimethoxybenzamide was obtained as powder. $^1$H NMR (d$_6$-DMSO, 90 MHz) δ/ppm=8.186 (d, J=11.9 Hz, 1H), 7.830 (t, J=8.3 Hz, 1H), 7.054 (d, J=3.6 Hz, 2H), 6.700 (t, J=3.6 Hz, 1H), 4.874 (t, J=8.3 Hz, 1H), 4.413 (m, 1H), 3.788 (s, 6H), 3.674 (m, 2H), 3.054 (m, 2H), 1.708-0.705 (m, 27H). $^{13}$C NMR (d$_6$-DMSO, 75 MHz) δ/ppm=170.345, 166.580, 160.946, 137.017, 106.150, 103.857, 62.361, 56.971, 56.120, 39.252, 31.979, 29.747, 29.701, 29.443, 29.398, 26.968, 22.778, 14.609. Anal. Calcd for C$_{26}$H$_{44}$N$_2$O$_5$ C, 67.21; H, 9.54; N, 6.03; O, 17.22. Found: C, 65.08; H, 9.59; N, 6.05; O, 17.23.

To synthesize (S)-2-acetamido-3-hydroxy-N-tetradecylpropanamide (Compound II-6), at 0° C. to the solution of 0.026 mL (0.48 mmol) of acetic acid in THF (50 ml), 32 mg (0.24 mmol) of HOBt and 0.10 g (0.24 mmol) of (S)-2-amino-3-hydroxy-N-tetradecylpropanamide were added. Then 53 mg (0.26 mmol) of DCC in 5 mL THF was added, and the pH was adjusted to 7-8 with 4-methylmorpholine. The reaction mixture was stirred at 0° C. for two hours, and at room temperature overnight. On evaporation the residue was dissolved in 80 mL of ethyl acetate. The solution was washed successively with saturated sodium bicarbonate, 5% potassium bisulfate, and saturated sodium chloride and the organic phase was separated and dried over anhydrous magnesium sulfate for two hours. After filtration and evaporation under reduced pressure crude product was obtained, and recrystallized using ethyl acetate to obtain 0.06 g (73.0%) of (S)-2-acetamido-3-hydroxy-N-tetradecylpropanamide as powder. $^1$H NMR (d$_6$-DMSO, 90 MHz) δ/ppm=7.730 (m, 2H), 4.775 (t, J=8.3 Hz, 1H), 4.155 (m, 1H), 3.495 (m, 2H), 3.020 (m, 2H), 1.846 (s, 3H), 1.7400.632 (m, 27H). $^{13}$C NMR (d$_6$-DMSO, 75 MHz) δ/ppm=168.538, 61.617, 56.849, 39.297, 31.964, 29.717, 29.686, 29.580, 29.382, 26.923, 22.763, 14.609.

General procedure for synthesis of nitro-, methyl-, chloro- and methoxy-substituted (S)-2-(benzylideneamino)-3-hydroxy-N-tetradecylpropanamide (Compounds II-7 through II-18): A mixture of 0.40 g (1.00 mmol) of (S)-2-amino-3-hydroxy-N-tetradecylpropanamide hydrochloride, 0.04 g (1.00 mmol) of NaOH, 1.00 mmol of substituted benzaldehyde, and 40 mL of methanol was stirred at room temperature for eight hours. The solvent was then evaporated under reduced pressure, and the residue was dissolved in 60 mL ethyl acetate. After filtration and evaporation, the residue was washed with 4×10 mL petroleum ether and 20 mL cooled methanol (4° C.) to yield substituted (S)-2-(benzylideneamino)-3-hydroxy-N-tetradecylpropanamide as powder.

(S)-2-(4-nitrobenzylideneamino)-3-hydroxy-N-tetradecylpropanamide (Compound II-7). Yield: 0.18 g (42%) as colorless powder. $^1$H NMR (d$_6$-DMSO, 300 MHz) δ/ppm=8.416 (s, 1H), 8.297 (d, J=8.7 Hz, 2H), 8.125 (d, J=8.7 Hz, 2H), 7.800 (t, J=5.7 Hz, 1H), 4.913 (t, J=6 Hz, 1H), 3.866 (m, 2H), 3.504 (m, 1H), 3.084 (m, 2H), 1.391 (m, 2H), 1.176 (m, 22H), 0.826 (t, J=6 Hz, 3H). $^{13}$C NMR (d$_6$-DMSO, 75 MHz) δ/ppm=169.996, 161.706, 149.362, 142.104, 131.339, 124.415, 76.466, 63.621, 39.115, 31.964, 29.808, 29.632, 29.686, 29.398, 26.999, 22.763, 14.609.

(S)-2-(3-nitrobenzylideneamino)-3-hydroxy-N-tetradecylpropanamide (Compound II-8). Yield: 0.22 g (51%) as colorless powder. $^1$H NMR (d$_6$-DMSO, 300 MHz) δ/ppm=8.671 (s, 1H), 8.421 (s, 1H), 8.291 (m, 2H), 7.784 (m, 2H), 4.907 (t, J=6 Hz, 1H), 3.869 (m, 2H), 3.520 (m, 1H), 3.081 (m, 2H), 1.389 (m, 2H), 1.176 (m, 22H), 0.825 (t, J=6 Hz, 3H). $^{13}$C NMR (d$_6$-DMSO, 75 MHz) δ/ppm=170.087, 161.539, 148.830, 138.126, 135.545, 130.929, 125.918, 123.003, 76.405, 63.636, 39.100, 31.964, 29.808, 29.671, 29.701, 29.382, 26.999, 22.778, 14.609.

(S)-2-(2-nitrobenzylideneamino)-3-hydroxy-N-tetradecylpropanamide (Compound II-9): Yield: 0.38 g (89%) as yellow powder. $^1$H NMR (d$_6$-DMSO, 300 MHz) δ/ppm=8.543 (s, 1H), 8.187 (d, J=7.5 Hz, 1H), 8.028 (d, J=7.5 Hz, 1H), 7.805 (t, J=7.5 Hz, 1H), 7.720 (t, J=7.5 Hz, 1H), 7.611 (t, J=5.7 Hz, 1H), 4.855 (t, J=6 Hz, 1H), 3.903 (dd, J=3.9 Hz, J=8.1 Hz, 1H), 3.793 (m, 1H), 3.506 (m, 1H), 3.084 (m, 2H), 1.397 (m, 2H), 1.198 (m, 22H), 0.832 (t, J=6 Hz, 3H). $^{13}$C NMR (d$_6$-DMSO, 75 MHz) δ/ppm=169.905, 159.018, 149.665, 142.104, 133.981, 132.295, 130.656, 124.764, 76.329, 63.636, 39.100, 31.979, 29.808, 29.701, 29.641, 29.382, 26.968, 22.778, 14.624.

(S)-2-(4-methylbenzylideneamino)-3-hydroxy-N-tetradecylpropanamide (Compound II-10). Yield: 0.24 g (60%) as colorless powder. $^1$H NMR (d6-DMSO, 300 MHz) δ/ppm=8.215 (s, 1H), 7.705 (m, 3H), 7.253 (d, J=8.1 Hz, 2H), 4.808 (t, J=6 Hz, 1H), 3.769 (m, 2H), 3.466 (m, 1H), 3.067 (m, 2H), 2.336 (s, 3H), 1.385 (m, 2H), 1.194 (m, 22H), 0.833 (t, J=6 Hz, 3H). $^{13}$C NMR (d$_6$-DMSO, 75 MHz) δ/ppm=170.588, 163.011, 141.405, 134.011, 129.775, 129.061, 76.254, 63.834, 39.024, 31.994, 29.823, 29.732, 29.413, 26.999, 22.778, 21.760, 14.609.

(S)-2-(3-methylbenzylideneamino)-3-hydroxy-N-tetradecylpropanamide (Compound II-11). Yield: 0.31 g (77%) as colorless powder. $^1$H NMR (d$_6$-DMSO, 300 MHz) δ/ppm=8.223 (s, 1H), 7.686 (m, 2H), 7.595 (d, J=7.2 Hz, 1H), 7.306 (m, 2H), 4.823 (t, J=6 Hz, 1H), 3.790 (m, 2H), 3.479 (m, 1H), 3.080 (m, 2H), 2.342 (s, 3H), 1.387 (m, 2H), 1.203 (m, 22H), 0.833 (t, J=6 Hz, 3H). $^{13}$C NMR (d$_6$-DMSO, 75 MHz) δ/ppm=170.542, 163.330, 138.445, 136.501, 132.250, 129.228, 129.107, 126.586, 76.345, 63.788, 39.024, 31.979, 29.808, 29.701, 29.398, 26.999, 22.778, 21.533, 14.624.

(S)-2-(2-methylbenzylideneamino)-3-hydroxy-N-tetradecylpropanamide (Compound II-12). Yield: 0.30 g (74%) as colorless powder. $^1$H NMR (d$_6$-DMSO, 300 MHz) δ/ppm=8.527 (s, 1H), 7.949 (d, J=7.5 Hz, 1H), 7.642 (d, J=5.7 Hz, 1H), 7.261 (m, 3H), 4.814 (t, J=6 Hz, 1H), 3.825 (m, 2H), 3.475 (m, 1H), 3.092 (m, 2H), 2.466 (s, 3H), 1.391 (m, 2H), 1.196 (m, 22H), 0.831 (t, J=6 Hz, 3H). $^{13}$C NMR (d$_6$-DMSO, 75 MHz) δ/ppm=170.573, 161.918, 138.399, 134.436, 131.384, 131.096, 128.272, 126.526, 76.694, 63.803, 39.024, 31.994, 29.838, 29.747, 29.428, 27.014, 22.793, 19.604, 14.594.

(S)-2-(4-chlorobenzylideneamino)-3-hydroxy-N-tetradecylpropanamide (Compound II-13). Yield: 0.37 g (87%) as colorless powder. $^1$H NMR (d$_6$-DMSO, 300 MHz) δ/ppm=8.264 (s, 1H), 7.870 (d, J=7.8 Hz, 2H), 7.741 (t, J=5.7 Hz, 1H), 7.506 (d, J=7.8 Hz, 2H), 4.870 (t, J=6 Hz, 1H), 3.809 (m, 2H), 3.463 (m, 1H), 3.065 (m, 2H), 1.382 (m, 2H), 1.188 (m, 22H), 0.829 (t, J=6 Hz, 3H). $^{13}$C NMR (d$_6$-DMSO, 75 MHz) δ/ppm=170.360, 162.040, 136.198, 135.393, 130.747, 129.304, 76.193, 63.712, 39.054, 31.979, 29.732, 29.398, 26.983, 22.778, 14.609.

(S)-2-(3-chlorobenzylideneamino)-3-hydroxy-N-tetradecylpropanamide (Compound II-14). Yield: 0.35 g (83%) as colorless powder. $^1$H NMR (d$_6$-DMSO, 300 MHz) δ/ppm=8.257 (s, 1H), 7.979 (s, 1H), 7.767 (m, 2H), 7.502 (m, 2H), 4.851 (t, J=6 Hz, 1H), 3.808 (m, 2H), 3.478 (m, 1H), 3.080 (m, 2H), 1.390 (m, 2H), 1.192 (m, 22H), 0.830 (t, J=6 Hz, 3H). $^{13}$C NMR (d$_6$-DMSO, 75 MHz) δ/ppm=170.239, 161.888, 138.612, 134.254, 131.278, 131.126, 128.272, 128.014, 76.314, 63.742, 39.069, 31.979, 29.838, 29.717, 29.398, 27.014, 22.778, 14.609.

(S)-2-(2-chlorobenzylideneamino)-3-hydroxy-N-tetradecylpropanamide (Compound II-15). Yield: 0.35 g (83%) as colorless powder. $^1$H NMR (d$_6$-DMSO, 300 MHz) δ/ppm=8.603 (s, 1H), 8.185 (d, J=7.5 Hz, 1H), 7.772 (t, J=5.7 Hz, 1H), 7.465 (m, 3H), 4.868 (t, J=6 Hz, 1H), 3.908 (dd, J=3.9 Hz, J=8.1 Hz, 1H), 3.802 (m, 1H), 3.478 (m, 1H), 3.083 (m, 2H), 1.390 (m, 2H), 1.194 (m, 22H), 0.834 (t, J=6 Hz, 3H). $^{13}$C NMR (d$_6$-DMSO, 75 MHz) δ/ppm=170.117, 159.231, 137.260, 134.998, 133.131, 130.458, 129.487, 127.983, 76.421, 63.545, 39.069, 31.979, 29.717, 29.398, 26.999, 22.778, 14.624.

(S)-2-(4-methoxybenzylideneamino)-3-hydroxy-N-tetradecylpropanamide (Compound II-16). Yield: 0.36 g (86%) as colorless powder. $^1$H NMR (d$_6$-DMSO, 300 MHz) δ/ppm=8.179 (s, 1H), 7.775 (d, J=9.0 Hz, 2H), 7.680 (t, J=5.7 Hz, 1H), 6.989 (d, J=9.0 Hz, 2H), 4.814 (t, J=6 Hz, 1H), 3.792 (s, 3H), 3.769 (m, 2H), 3.443 (m, 1H), 3.074 (m, 2H), 1.381 (m, 2H), 1.192 (m, 22H), 0.832 (t, J=6 Hz, 3H). $^{13}$C NMR (d$_6$-DMSO, 75 MHz) δ/ppm=170.755, 162.465, 162.116, 130.732, 129.426, 114.576 76.178, 63.909, 55.984, 39.009, 31.979, 29.808, 29.717, 29.398, 26.983, 22.778, 14.624.

(S)-2-(3-methoxybenzylideneamino)-3-hydroxy-N-tetradecylpropanamide (Compound II-17). Yield: 0.36 g (86%) as colorless powder. $^1$H NMR (d$_6$-DMSO, 300 MHz) δ/ppm=8.234 (s, 1H), 7.719 (t, J=5.7 Hz, 1H), 7.422 (s, 1H), 7.354 (m, 2H), 7.048 (m, 1H), 4.857 (t, J=6 Hz, 1H), 3.790 (m, 5H), 3.480 (m, 1H), 3.081 (m, 2H), 1.364 (m, 2H), 1.192 (m, 22H), 0.833 (t, J=6 Hz, 3H). $^{13}$C NMR (d$_6$-DMSO, 75 MHz) δ/ppm=170.482, 163.148, 160.142, 137.974, 130.306, 121.986, 117.659, 113.286, 76.284, 63.742, 55.893, 39.039, 31.979, 29.701, 29.398, 26.999, 22.778, 14.609.

(S)-2-(2-methoxybenzylideneamino)-3-hydroxy-N-tetradecylpropanamide (Compound II-18). Yield: 0.30 g (72%) as colorless powder. $^1$H NMR (d$_6$-DMSO, 300 MHz) δ/ppm=8.576 (s, 1H), 8.014 (d, J=7.8 Hz, 1H), 7.698 (t, J=5.7 Hz, 1H), 7.443 (t, J=7.8 Hz, 1H), 7.089 (d, J=7.8 Hz, 1H), 6.983 (t, J=7.8 Hz, 1H), 4.796 (t, J=6 Hz, 1H), 3.835 (s, 3H), 3.784 (m, 2H), 3.451 (m, 1H), 3.073 (m, 2H), 1.384 (m, 2H), 1.196 (m, 22H), 0.834 (t, J=6 Hz, 3H). $^{13}$C NMR (d$_6$-DMSO, 75 MHz) δ/ppm=170.603, 159.291, 158.289, 133.161, 127.892, 124.355, 121.014, 112.375, 76.709, 63.818, 56.272, 39.009, 31.979, 29.808, 29.717, 29.398, 26.983, 22.778, 14.624.

General procedure for synthesis of hydroxy-substituted (S)-2-(benzylideneamino)-3-hydroxy-N-tetradecylpropanamide (Compounds II-19, II-20, and II-21): A mixture of 0.40 g (1.00 mmol) of (S)-2-amino-3-hydroxy-N-tetradecylpropanamide hydrochloride, 0.04 g (1.00 mmol) of NaOH, 1.00 mmol of hydroxybenzaldehyde, and 40 mL of methanol was stirred at room temperature for eight hours. The solvent was then evaporated under reduced pressure, and the residue was washed with cooled methanol to yield (S)-2-(hydroxybenzylideneamino)-3-hydroxy-N-tetradecylpropanamide as powder.

(S)-2-(4-hydroxybenzylideneamino)-3-hydroxy-N-tetradecylpropanamide (Compound II-19). Yield: 0.20 g (50%) as colorless powder. $^1$H NMR (d$_6$-DMSO, 300 MHz) δ/ppm=8.114 (s, 1H), 7.639 (m, 3H), 6.806 (d, J=8.1 Hz, 2H), 4.768 (t, J=6 Hz, 1H), 3.739 (m, 2H), 3.429 (m, 1H), 3.070 (m, 2H), 1.381 (m, 2H), 1.201 (m, 22H), 0.834 (t, J=6 Hz, 3H). $^{13}$C NMR (d$_6$-DMSO, 75 MHz) δ/ppm=170.846, 162.617, 160.734, 130.868, 127.953, 115.958, 76.132, 63.955, 39.994, 31.979, 29.797, 29.717, 29.382, 26.983, 22.778, 14.624.

(S)-2-(3-hydroxybenzylideneamino)-3-hydroxy-N-tetradecylpropanamide (Compound II-20). Yield: 0.21 g (52%) as colorless powder. $^1$H NMR (d$_6$-DMSO, 300 MHz) δ/ppm=8.166 (s, 1H), 7.635 (t, J=5.7 Hz, 1H), 7.235 (m, 3H), 6.860 (m, 1H), 3.783 (m, 2H), 3.464 (m, 1H), 3.075 (m, 2H), 1.385 (m, 2H), 1.202 (m, 22H), 0.834 (t, J=6 Hz, 3H). $^{13}$C NMR (d$_6$-DMSO, 75 MHz) δ/ppm=170.497, 163.406, 158.365, 137.883, 130.170, 120.255, 118.782, 115.123, 76.223, 63.773, 39.039, 31.994, 29.853, 29.732, 29.413, 27.014, 22.793, 14.624.

(S)-2-(2-hydroxybenzylideneamino)-3-hydroxy-N-tetradecylpropanamide (Compound II-21). Yield: 0.15 g (37%) as yellow powder. $^1$H NMR (d$_6$-DMSO, 300 MHz) δ/ppm=8.468 (s, 1H), 7.924 (t, J=5.7 Hz, 1H), 7.473 (d, J=7.5 Hz, 1H), 7.322 (t, J=7.5 Hz, 1H), 6.882 (m, 2H), 4.926 (br, 1H), 3.918 (dd, J=4.5 Hz, J=7.8 Hz, 1H), 3.777 (dd, J=4.5 Hz, J=10.8 Hz, 1H), 3.569 (m, 1H), 3.050 (m, 2H), 1.373 (m, 2H), 1.195 (m, 22H), 0.835 (t, J=6 Hz, 3H). $^{13}$C NMR (d$_6$-DMSO, 75 MHz) δ/ppm=169.571, 167.278, 161.022, 133.115, 132.478, 119.587, 119.238, 117.127, 75.115, 63.408, 39.176, 31.979, 29.717, 29.656, 29.398, 26.983, 22.778, 14.624.

General procedure for synthesis of substituted (S)-2-(benzylamino)-3-hydroxy-N-tetradecyl propanamide (Compounds II-22 through II-25): To the solution of 0.20 mmol substituted (S)-2-(benzylideneamino)-3-hydroxy-N-tetradecylpropanamides II-9, II-15, II-18, and II-21 in 10 mL of methanol, 20 mg (0.54 mmol) of NaBH$_4$ was added. The reaction mixture was stirred at room temperature for 10 h, and evaporated under vacuum. The residue was purified by thin layer chromatography to give substituted (S)-2-(benzylamino)-3-hydroxy-N-tetradecylpropanamide II-22 to II-25 as colorless powder in 65.6-78.2% yields.

(S)-2-(2-nitrobenzylamino)-3-hydroxy-N-tetradecylpropanamide (Compound II-22). Yield: 75.3%, colorless powder. GC/MS (m/e): 435 M+, 418 [M−.OH]+, $^1$H NMR (d$_6$-DMSO, 300 MHz) δ/ppm=7.926 (d, J=3.6 Hz, 1H), 7.720 (m, 3H), 7.500 (t, J=8.4 Hz, 1H), 4.720 (t, J=5.4 Hz, 1H), 3.977 (d, J=15.3 Hz, 1H), 3.847 (d, J=15.3 Hz, 1H), 3.462 (m, 2H), 3.021 (m, 3H), 1.359 (m, 2H), 1.209 (m, 24H), 0.833 (t, J=6.6 Hz, 3H). $^{13}$C NMR (d$_6$-DMSO, 75 MHz) δ/ppm=172.243, 137.245, 135.803, 133.844, 131.415, 128.834, 124.947, 64.608, 63.120, 48.741, 38.963, 31.979, 29.732, 29.671, 29.382, 27.014, 22.778, 14.609. Anal. Calcd for $C_{24}H_{41}N_3O_4$: C, 66.17; H, 9.49; N, 9.65; O, 14.69. Found: C, 66.60; H, 9.69; N, 9.54; O, 14.33.

(S)-2-(2-chlorobenzylamino)-3-hydroxy-N-tetradecyl-propanamide (Compound II-23). Yield: 73.4%, colorless powder. GC/MS (m/e): 424 M+, $^1$H NMR (CDCl$_3$, 300 MHz) δ/ppm=7.404~7.233 (m, 5H), 3.899 (s, 2H), 3.794 (t, J=5.1 Hz, 2H), 3.237 (t, J=5.7 Hz, 3H), 1.633 (m, 2H), 1.492 (t, J=6.9 Hz, 2H), 1.257 (m, 24H), 0.882 (t, J=6.9 Hz, 3H). $^{13}$C NMR (CDCl$_3$, 75 MHz) δ/ppm=136.319, 130.641, 130.048, 129.168, 127.270, 114.971, 63.180, 62.922, 50.639, 39.312, 32.145, 29.868, 29.762, 29.579, 29.504, 27.150, 22.899, 14.335. Anal. Calcd for $C_{24}H_{41}ClN_2O_2$: C, 67.82; H, 9.72; N, 6.59; O, 7.53. Found: C, 67.58; H, 9.93; N, 6.69; O, 9.72.

(S)-2-(2-methyoxybenzylamino)-3-hydroxy-N-tetrade-cylpropanamide (Compound II-24). Yield: 78.2%, colorless powder. GC/MS (m/e): 319 [M−H]+, $^1$H NMR (CDCl$_3$, 300 MHz) δ/ppm=7.359-6.906 (m, 5H), 4.076 (dd, J=3.0 Hz, J=11.1 Hz, 1H), 3.855 (s, 3H), 3.758 (m, 2H), 3.590 (m, 1H), 3.250 (m, 2H), 2.247 (m, 1H), 1.501 (m, 2H), 1.254 (m, 24H), 0.880 (t, J=6.9 Hz, 3H). $^{13}$C NMR (CDCl$_3$, 75 MHz) δ/ppm=136.319, 130.641, 130.048, 129.168, 127.270, 114.971, 63.180, 62.922, 52.203, 50.639, 39.312, 32.145, 29.868, 29.762, 29.579, 29.504, 27.150, 22.899, 14.335. Anal. Calcd for $C_{25}H_{44}N_2O_3$: C, 71.39; H, 10.54; N, 6.66; O, 11.41. Found: C, 71.30; H, 9.82; N, 6.90; O, 11.81.

(S)-2-(2-hydroxybenzylamino)-3-hydroxy-N-tetradecyl-propanamide (Compound II-25). Yield: 75.3%, colorless powder. GC/MS (m/e): 405 [M−H]+, 389 [M−.OH]+, $^1$H NMR (CDCl$_3$, 300 MHz) δ/ppm=7.188 (t, J=7.5 Hz, 1H), 6.985 (d, J=7.5 Hz, 1H), 6.846 (d, J=7.5 Hz, 1H), 6.799 (t, J=7.5 Hz, 1H), 6.196 (br, 1H), 4.090 (d, J=14.1 Hz, 1H), 3.839 (m, 2H), 3.757 (dd, J=5.4 Hz, J=11.1 Hz, 1H), 3.281 (m, 2H), 3.142 (t, J=5.4 Hz, 1H), 1.513 (t, J=6.6 Hz, 2H), 1.262 (m, 24H), 0.882 (t, J=6.6 Hz, 3H). $^{13}$C NMR (CDCl$_3$, 75 MHz) δ/ppm=159.003, 129.396, 129.198, 122.335, 119.815, 116.702, 62.953, 61.283, 50.578, 39.859, 32.145, 29.868, 29.807, 29.716, 29.579, 29.473, 27.089, 22.899, 14.335. Anal. Calcd for $C_{24}H_{42}N_2O_3$: C, 70.89; H, 10.41; N, 6.89; O, 11.80. Found: C, 70.29; H, 10.99; N, 6.86; O, 11.92.

Cell Cultures.

Human cancer cell lines derived from breast, MCF-7, endocrine-resistant MDA-MB-231, and chemoresistant MCF-7TN-R were cultured in 75 cm$^2$ culture flasks in DMEM (Invitrogen, Co.) supplemented with 10% FBS (Life Technologies, Inc., Gaithersburg, Md.), basic minimum MEM essential (50×, Invitrogen Co.) and MEM non-essential (100×, Invitrogen, Co.) amino acids, sodium pyruvate (100× Invitrogen Co.), antimicotic-antibiotic (10,000 U/mL penicillin G sodium; 10,000 µg/mL streptomycin sulphate; 25 µg/mL amphotericin B as Fungizone®), and human recombinant insulin (4 mg/mL Invitrogen Co). Culture flasks were maintained in a tissue culture incubator in a humidified atmosphere of 5% $CO_2$ and 95% air at 37° C.

Clonogenic Survival Assay.

MCF-7, MDA-MB-231, or MCF-7TN-R cells were plated in 6-well plates at 1000 cells per well. Twenty-four hours later, cells were treated with varying concentrations of the compound and then monitored microscopically for colony growth. Ten days later the cells were fixed with 3% glutaraldehyde. Following fixation for 15 min, the plates were washed and stained with a 0.4% solution of crystal violet in 20% methanol for 30 min, washed with PBS, and air-dried. Colonies of 30 cells were counted as positive. Results are normalized to percent clonogenic survival from untreated control cells. Statistical analysis of $IC_{50}$ values were calculated from concentration-response curves using GraphPad Prism 5.0 (Graphpad Software, San Diego, Calif.), using with the equation:

$$Y=\text{Bottom}+(\text{Top}-\text{bottom})/1+10 \text{ Log EC50}-X.$$

Viability Assay Using MTT.

The effect of ceramide and compounds on cell growth was determined using MTT viability assays. MCF-7, MDA-MB-231, or MCF-7TN-R cells were plated at 7.5×10$^5$ cells per well in a 96-well plate in phenol-free DMEM supplemented with 5% FBS and allowed to adhere overnight. Cells were then treated with compounds I-1, I-2, I-3, or I-4 (ranging from 0.1 to 100 µM) for 24 h. Following that treatment, 20 µL of MTT (5 mg/ml) reagent was added to each well prior to incubation for 4 hr. Cells were then lysed with 20% SDS in 50% dimethylformamide. The pH and absorbances were read on an EL×808 Microtek plate reader (Winooski, Vt.) at 550 nm, with a reference wavelength of 630 nm.

Apoptosis ELISA Assay.

The induction of apoptosis by compounds was assayed using the nucleosome ELISA kit (Roche). The kit quantified formation of cytoplasmic histone-associated oligonucleosome DNA fragments resulting from apoptosis. MCF-7, MDA-MB-231, or MCF-7TN-R cells were plated at 7500 cell per well in 96-well plates and treated for 24 hours with double the $IC_{50}$ value concentrations of the ceramide (8.3 µM) and II-3 (9.4 µM). The induction of apoptosis was determined by the amount of nucleosomes in the cytoplasm per the manufacturer's protocol. The values are the mean±SE of three independent experiments.

Effect on Cellular Sphingolipid Species Using Lipidomics Analysis.

(A) MCF-7, (B) MDA-MB-231, and (C) MCF-7TN-R cells were treated with ceramide (10 µM) and II-3 (10 µM) for 24 h. The values are the mean±SE of two independent experiments. S2 Endogenous lipid levels were quantified by mass spectrometry (Lipidomics Core, Medical University of South Carolina) according to published methods. Briefly, cells were collected, fortified with internal standards and extracted with ethyl acetate/isopropyl alcohol. ESI/MS/MS analyses of sphingoid bases, sphingoid base 1-phosphates, ceramides, and sphingomyelins were performed on a Thermo Finnigan TSQ 7000 triple quadrupole mass spectrometer.

Statistical Analysis.

Statistical analysis of $IC_{50}$ values were calculated from concentration-response curves using GraphPad Prism 5.0 (Graphpad Software, San Diego, Calif.), using with the equation:

$$Y=\text{Bottom}+(\text{Top}-\text{bottom})/1+10 \text{ Log EC50}-X$$

assuming a standard slope, where the response goes from 10% to 90% of maximal as X increases over two log units. Differences in $IC_{50}$ were compared using Student's unpaired t-test with p<0.05 as the limit of statistical significance. Experiments comparing multiple concentrations to the control were tested with one-way ANOVA with Bonferroni posttest to compare individual concentrations. All statistical analysis were done using GraphPad Prism 5.0. All statistical analysis was done using GraphPad Prism 5.0.

The tables below show the $IC_{50}$ values of the indicated compounds for (1A) viability assays and (1B) clonogenic survival assays from experiments shown in FIGS. 1 through 5.

TABLE 1A

Viability Assays

| Compound | MDA-MB-231 ($IC_{50}$) | MCF-7TN-R ($IC_{50}$) | MCF-7 ($IC_{50}$) |
|---|---|---|---|
| I-1 | 5.4 | 2.4 | 22.6 |
| I-2 | 3.7 | 3.0 | 6.3 |
| I-3 | 4.8 | 3.6 | 9.0 |
| I-4 | 8.0 | 4.2 | 13.5 |

TABLE 1B

Clonogenic Survival Assays

| Compound | MDA-MB-231 ($IC_{50}$) | MCF-7TN-R ($IC_{50}$) | MCF-7 ($IC_{50}$) |
|---|---|---|---|
| I-1 | 1.6 | 0.7 | 1.5 |
| I-2 | 1.1 | 0.6 | 1.5 |
| I-3 | 1.4 | 0.1 | 1.7 |
| I-4 | 0.5 | 0.6 | 1.5 |

Figures 5A, 5B:
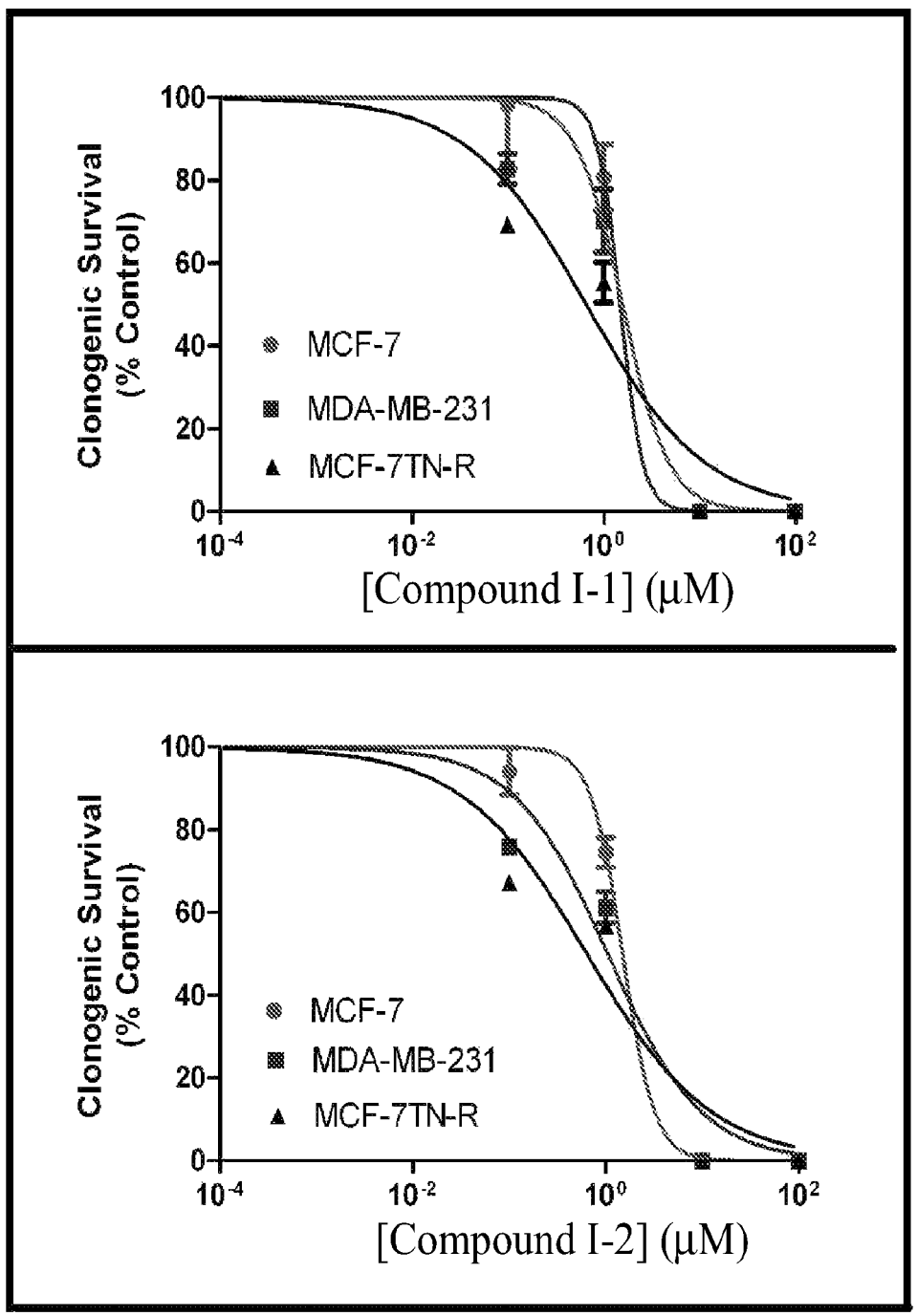
FIG. 5 shows the effect of compounds I-1, I-2, I-3, and I-4 on clonogenic survival of breast cancer cell lines MCF-7, endocrine resistant MDA-MB-231, and chemoresistant MCF-7-TNR.
Figures 5C, 5D:
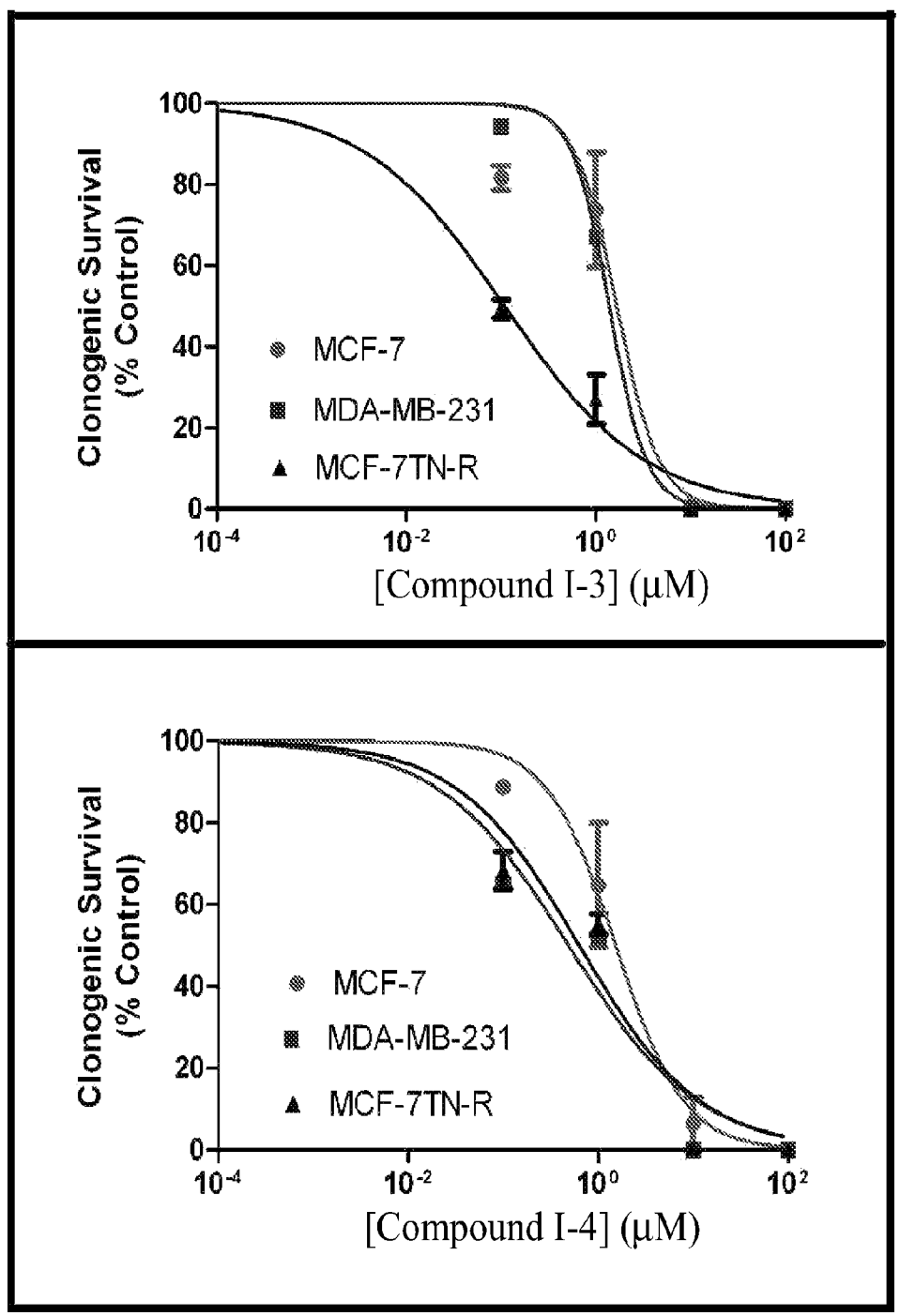
Figure 6:
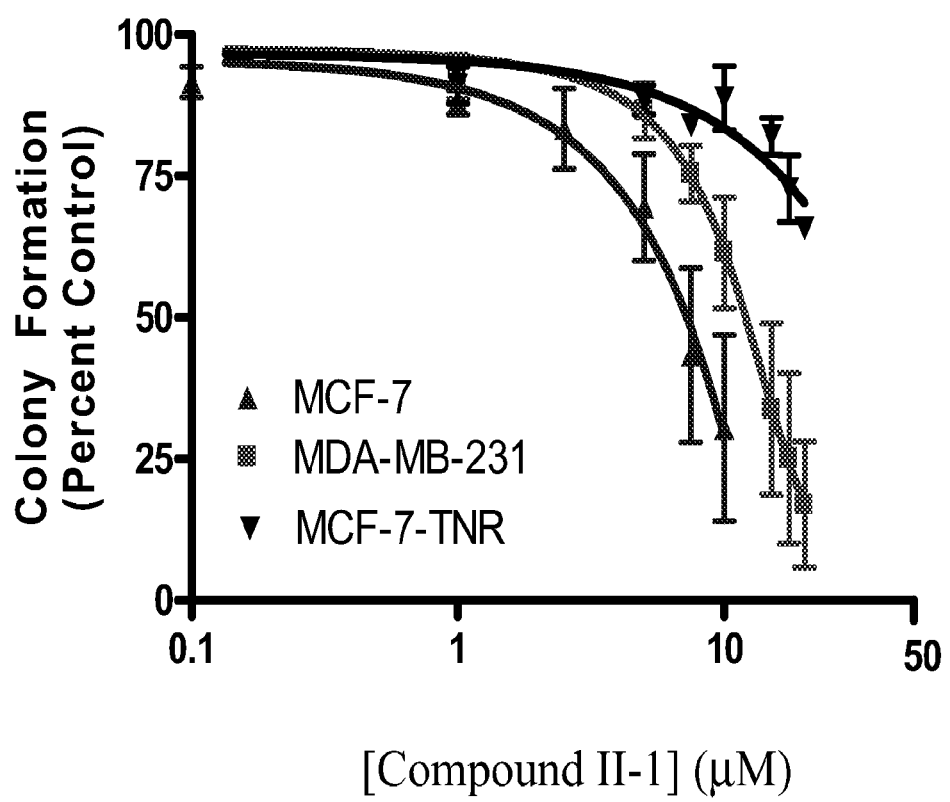
FIG. 6 demonstrates the inhibitory effect of compound II-1 on breast cancer cell lines MCF-7, endocrine resistant MDA-MB-231, and chemoresistant MCF-7-TNR.
Figure 7:
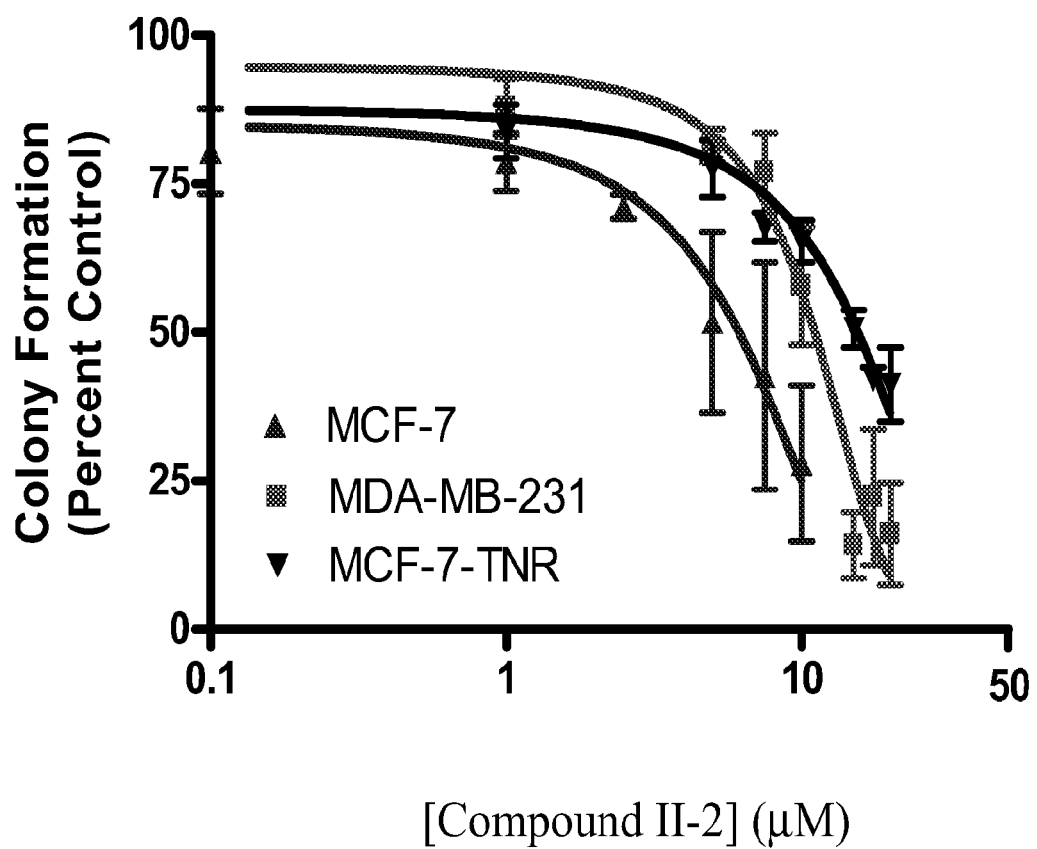
FIG. 7 demonstrates the inhibitory effect compound II-2 on breast cancer cell lines MCF-7, endocrine resistant MDA-MB-231, and chemoresistant MCF-7-TNR.
Figure 8:
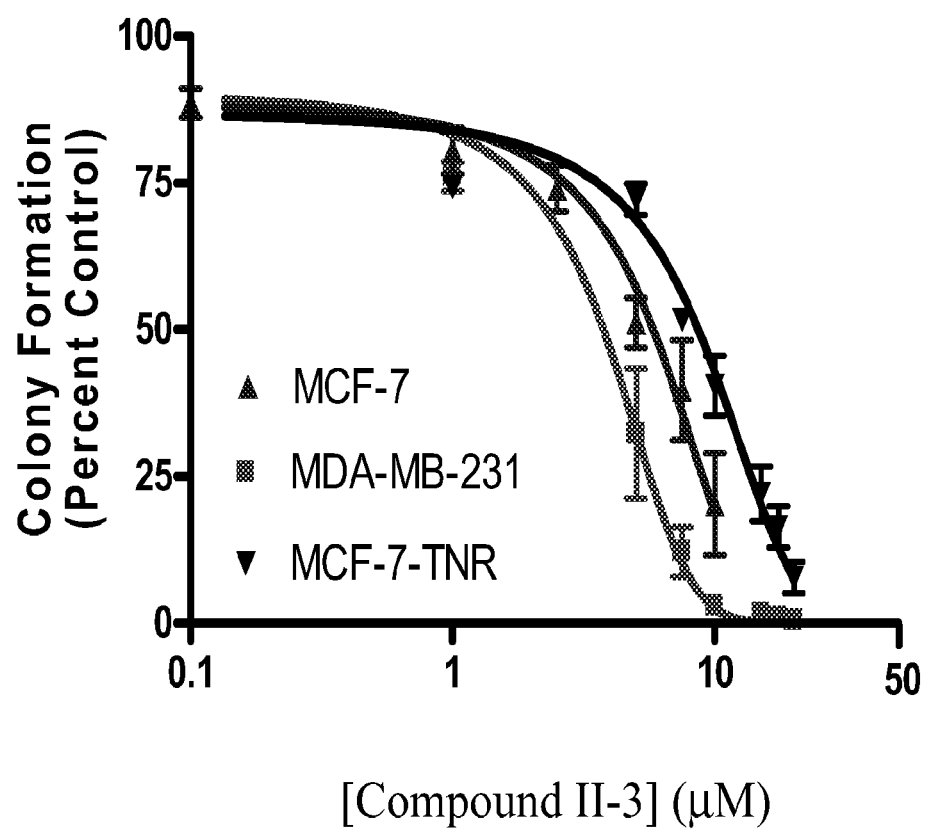
FIG. 8 demonstrates the inhibitory effect of compound II-3 on breast cancer cell lines MCF-7, endocrine resistant MDA-MB-231, and chemoresistant MCF-7-TNR.
Figure 9:
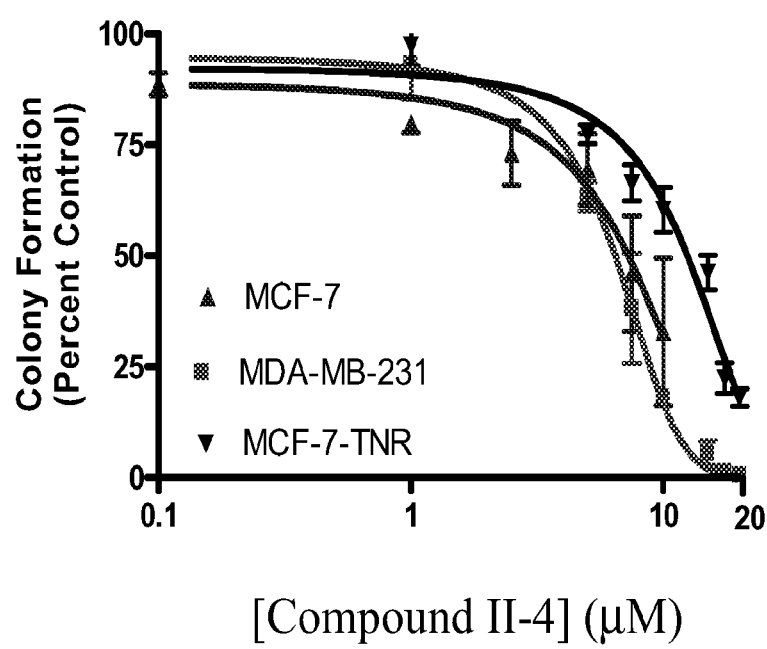
FIG. 9 demonstrates the inhibitory effect of compound II-4 on breast cancer cell lines MCF-7, endocrine resistant MDA-MB-231, and chemoresistant MCF-7-TNR.
Figure 10:
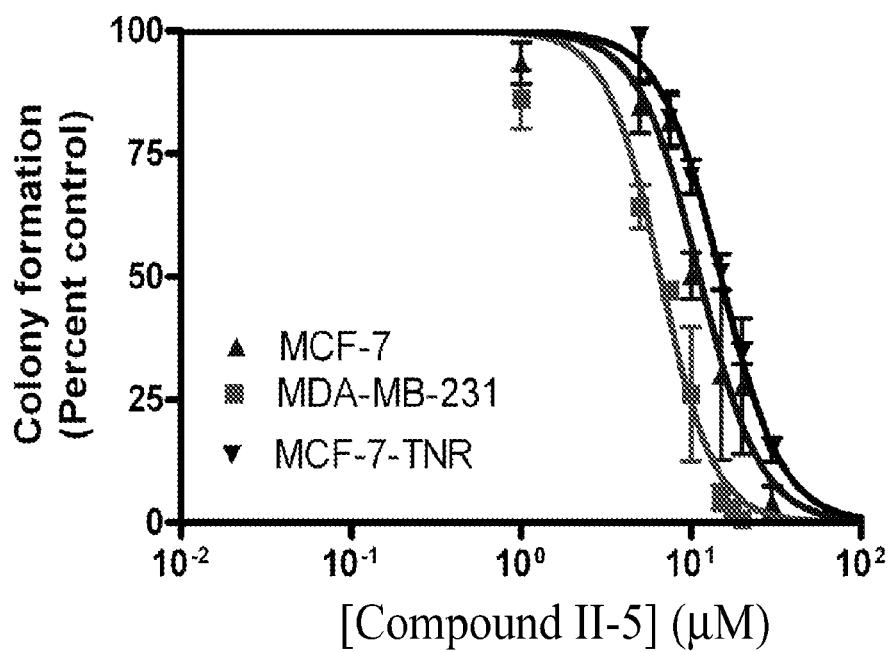
FIG. 10 demonstrates the inhibitory effect of compound II-5 on breast cancer cell lines MCF-7, endocrine resistant MDA-MB-231, and chemoresistant MCF-7-TNR.
Figure 11:
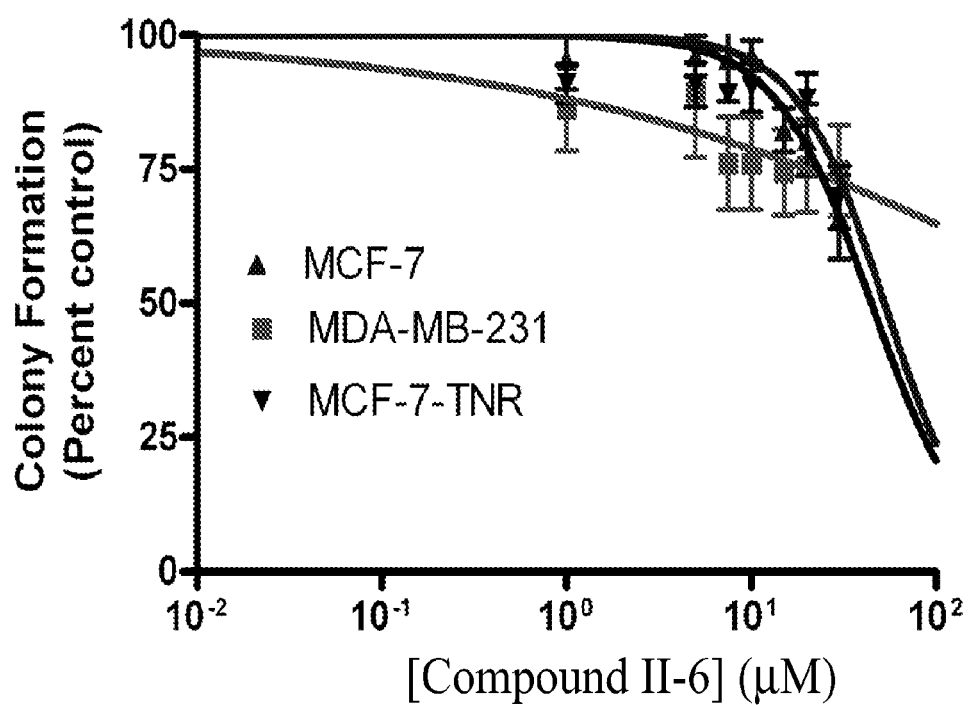
FIG. 11 demonstrates the inhibitory effect of compound II-6 on breast cancer cell lines MCF-7, endocrine resistant MDA-MB-231, and chemoresistant MCF-7-TNR.
Figure 12:
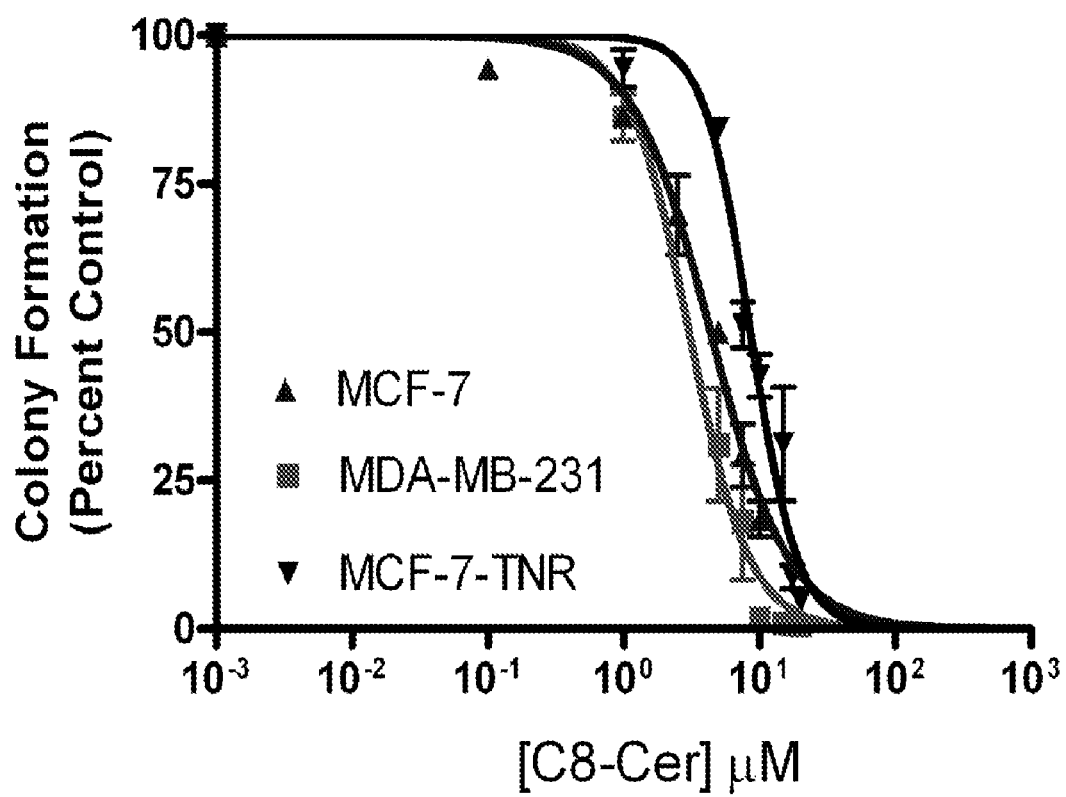
FIG. 12 demonstrates the inhibitory effect of C8-Cer on breast cancer cell lines MCF-7, endocrine resistant MDA-MB-231, and chemoresistant MCF-7-TNR.
Figure 13:
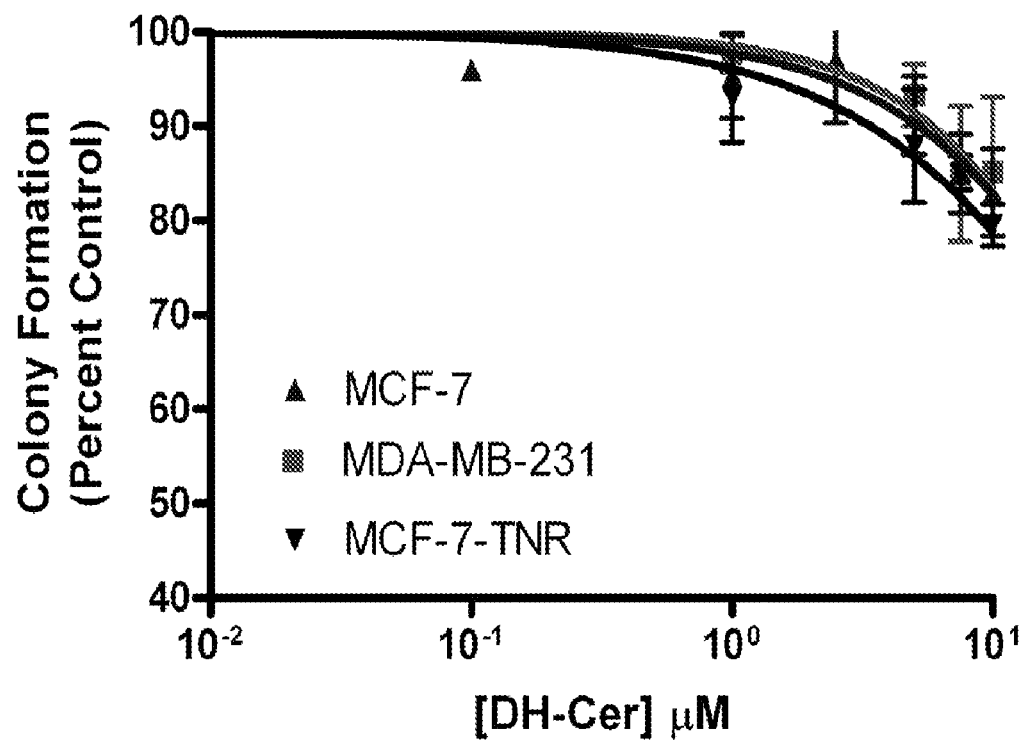
FIG. 13 demonstrates the inhibitory effect of DH-Cer on breast cancer cell lines MCF-7, endocrine resistant MDA-MB-231, and chemoresistant MCF-7-TNR.

The effects of compounds I-1, I-2, I-3, and I-4 on clonogenic survival are shown in FIG. 5. The four compounds displayed increased efficacy in blocking survival compared to viability in all three breast cancer cell lines. Interestingly, the compounds were most effective in the chemoresistant MCF-7TN-R cell line, with compound I-3 displaying an $IC_{50}$ of 0.1 µM.

The four compounds were effective in diminishing chemoresistant and endocrine resistant breast cancer cell viability and survival. Compounds I-1 and I-3 display the lowest $IC_{50}$ values for the viability and survival assays for MCF-7TN-R, respectively. Compound I-3 is substantially more effective than the other compounds in decreasing chemoresistant breast cancer cell survival. This increased efficacy may be due to the presence of the imine functional group in Compound I-3. This functional group is believed not to be hydrolyzed by the enzyme ceramidase, effectively blocking the production of sphingosine and preventing compound depletion.

Compounds II-1, II-2, II-3, II-4, II-5, and II-6 were compared for their inhibitory effect on breast cancer clonogenic survival. Cells were treated with varying concentration of compound, ranging from 0.1 µM-20 µM for 10 days. The data displayed in FIGS. 6-13 are the mean±SD of three independent experiments. At endpoint, cell colonies were fixed, stained and recorded as percent vehicle control. The $IC_{50}$ values for compounds II-1 to II-6 are listed in Table 2; DH-Cer and C8-Cer were also tested and are listed in Table 2. Compounds II-1 to II-6 displayed anti-survival properties in both drug resistant and sensitive breast cancer.

TABLE 2

| | MCF-7 ($IC_{50}$) | MDA-MB-231 ($IC_{50}$) | MCF-7-TNR ($IC_{50}$) |
|---|---|---|---|
| DH-Cer | 31.7 | 41.4 | 49.6 |
| C8-Cer | 4.2 | 3.0 | 8.6 |
| Compound II-1 | 7.2 | 11.5 | 23.5 |
| Compound II-2 | 5.0 | 10.5 | 15.2 |
| Compound II-3 | 4.7 | 2.4 | 7.7 |
| Compound II-4 | 6.7 | 6.1 | 11.1 |
| Compound II-5 | 11.2 | 6.6 | 15.0 |
| Compound II-6 | 44.7 | 75.1 | 52.7 |

Compounds II-1, II-2, II-3, II-4, II-5, and II-6 showed biological activity in the MCF-7 cell line. Compound II-2 and compound II-3, both missing the original amide carbonyl group, had the greatest efficacy in MCF-7 cells, with $IC_{50}$ values of 4.97 µM and 4.69 µM, respectively. Interestingly, these two compounds also showed activity in endocrine resistant MDA-MB-231 cells and chemoresistant MCF-7-TNR cells as well. Compound II-3 appeared most potent compound and more effective than C8-ceramide in treating drug resistant breast cancer, with $IC_{50}$ values of 2.35 µM in MDA-MB-231 cells and 7.67 µM in MCF-7-TNR cells.

Figure 14:
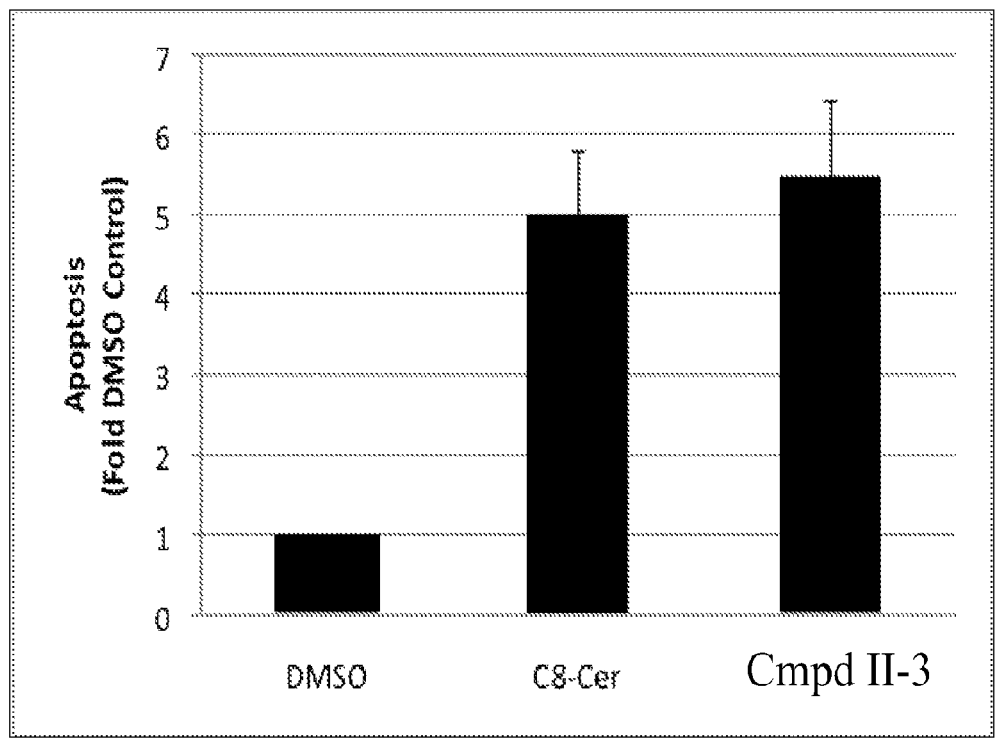
FIG. 14 demonstrates the effect of compound II-3 on breast cancer apoptosis.

The ability of compound II-3 to induce apoptosis in MCF-7 cells was tested. Using a Cell Death Detection ELISA (Roche) to assess apoptosis, $IC_{50}$ was measured for compound II-3 and C8-ceramide. As seen in FIG. 14, compound II-3 caused a 5.4 fold induction (p=0.034) in apoptosis compared to a 5.0 fold induction caused by C8-ceramide (p=0.008).

Figure 15:
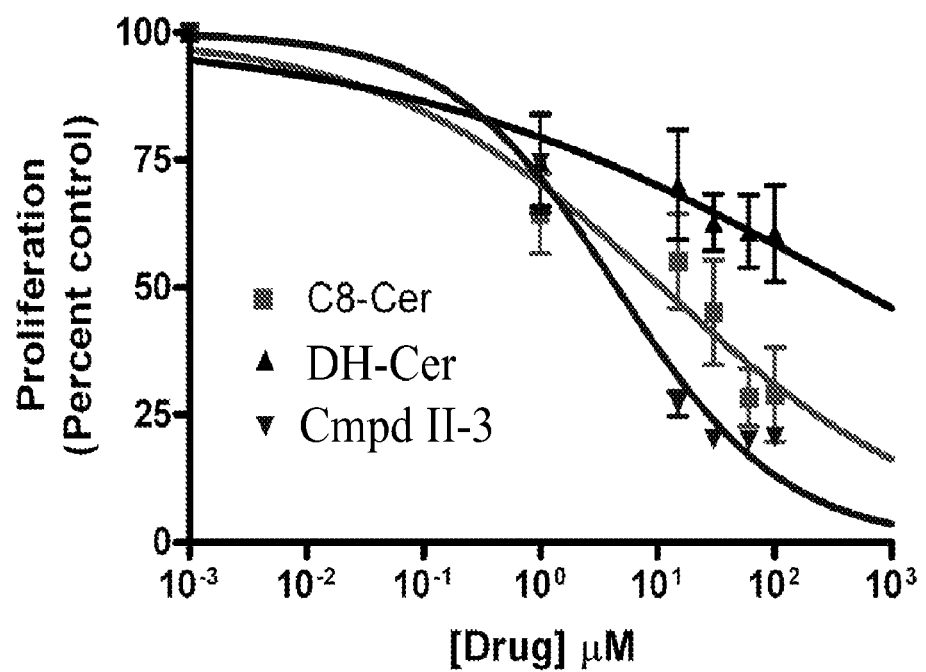
FIG. 15 demonstrates the effect of compound II-3, DH-Cer, and C8-Cer on breast cancer proliferation in the MCF-7 cell line.
Figure 16:
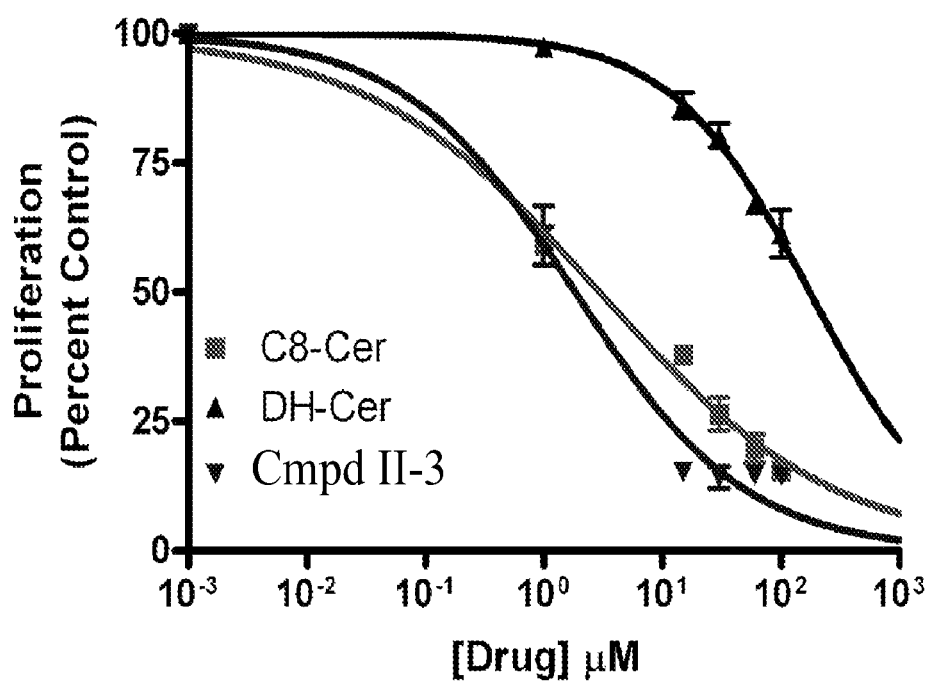
FIG. 16 demonstrates the effect of compound II-3, DH-Cer, and C8-Cer on breast cancer proliferation in the MDA-MB-231 cell line.
Figure 17:
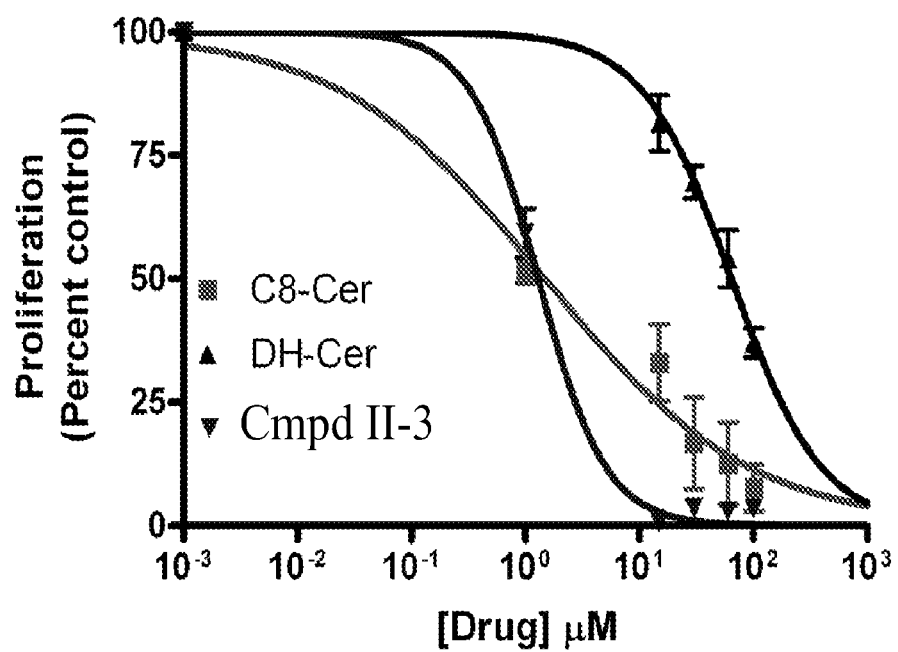
FIG. 17 demonstrates the effect of compound II-3, DH-Cer, and C8-Cer on breast cancer proliferation in the MCF-7TN-R cell line.

The ability of compound II-3 to block proliferation as an anti-survival mechanism in addition to apoptosis was determined by measuring anti-proliferative effects. Compound II-3 has a greater anti-proliferative effect than C8-ceramide in MCF-7, MDA-MB-231, and MCF-7TN-R cell lines, with $IC_{50}$ values of 4.5 µM, 1.8 µM, and 1.2 µM, respectively (FIGS. 15-17).

Figure 18:
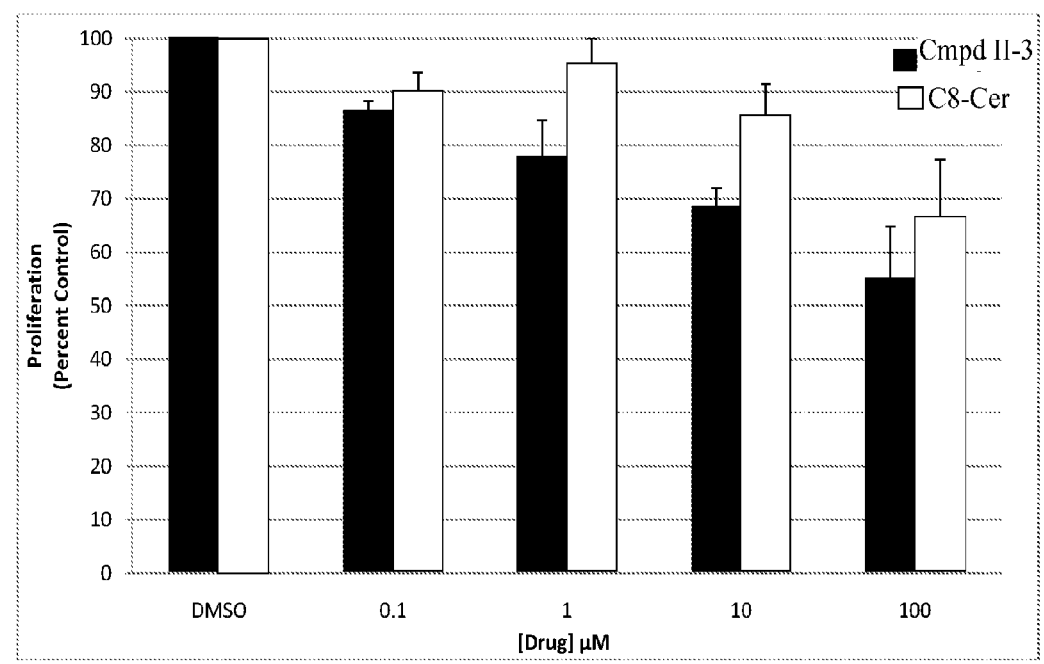
FIG. 18 demonstrates the effect of compound II-3 and C8-Cer on MCF10A (normal breast epithelial) cell proliferation. MCF10A cells were treated with varying concentrations of drug (0.1-100 μM) for 24 h. The values are the mean±SE of four independent experiments.

The selectivity of compound II-3 and C8-ceramide to inhibit cell growth of cancer cells was determined by performing proliferation assays using MCF10A (normal breast epithelial) cells (FIG. 18). Both compound II-3 and C8-ceramide showed little effect on normal breast epithelial proliferation, even at 100 µM, which is greater than 50 fold of the $IC_{50}$ value in chemoresistant cells.

Figure 19:
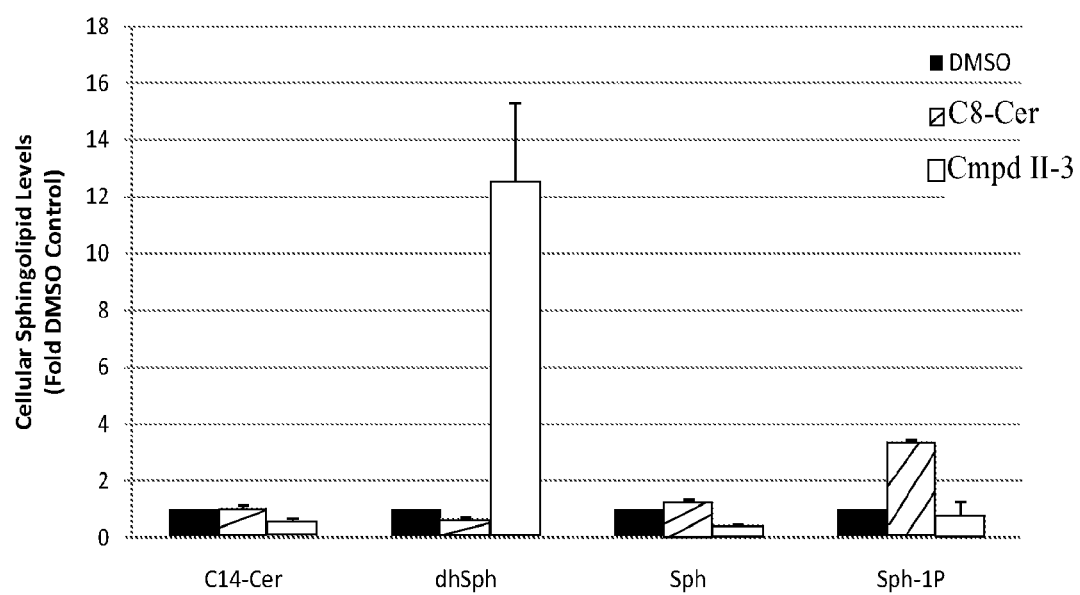
FIG. 19 demonstrates the effect of compound II-3, DH-Cer, and C8-Cer on the cellular sphingolipid species in the MCF-7 cell line.
Figure 20:
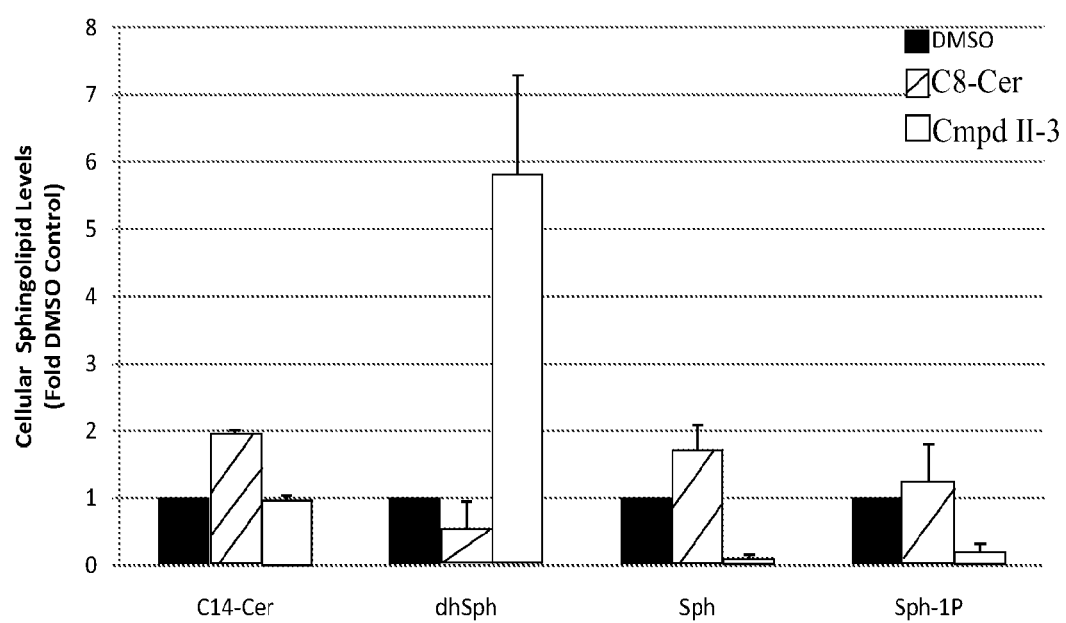
FIG. 20 demonstrates the effect of compound II-3, DH-Cer, and C8-Cer on the cellular sphingolipid species in the MDA-MB-231 cell line.
Figure 21:
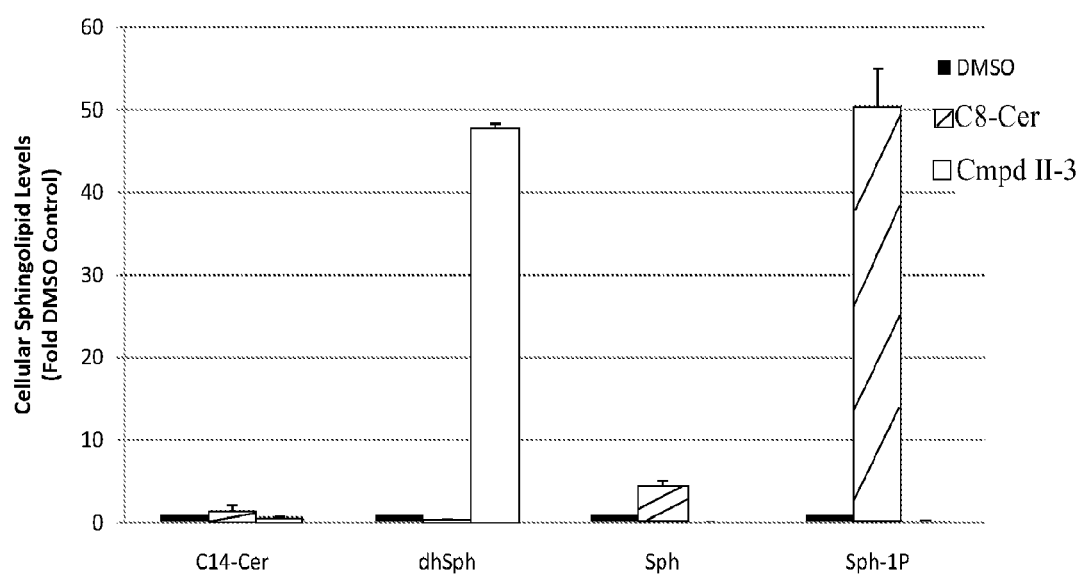
FIG. 21 demonstrates the effect of compound II-3, DH-Cer, and C8-Cer on the cellular sphingolipid species in the MCF-7TN-R cell line.
Figure 22:
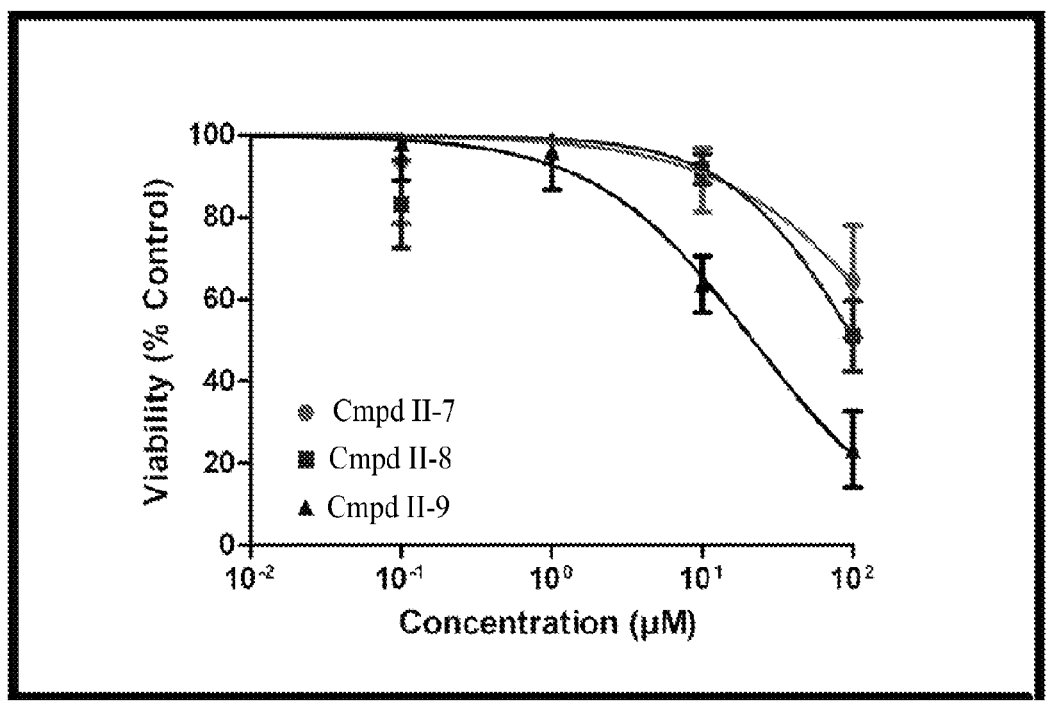
FIGS. 22-27 show the effect of compounds II-7 to II-25 on proliferation of MCF-7TN-R cells.
Figure 23:
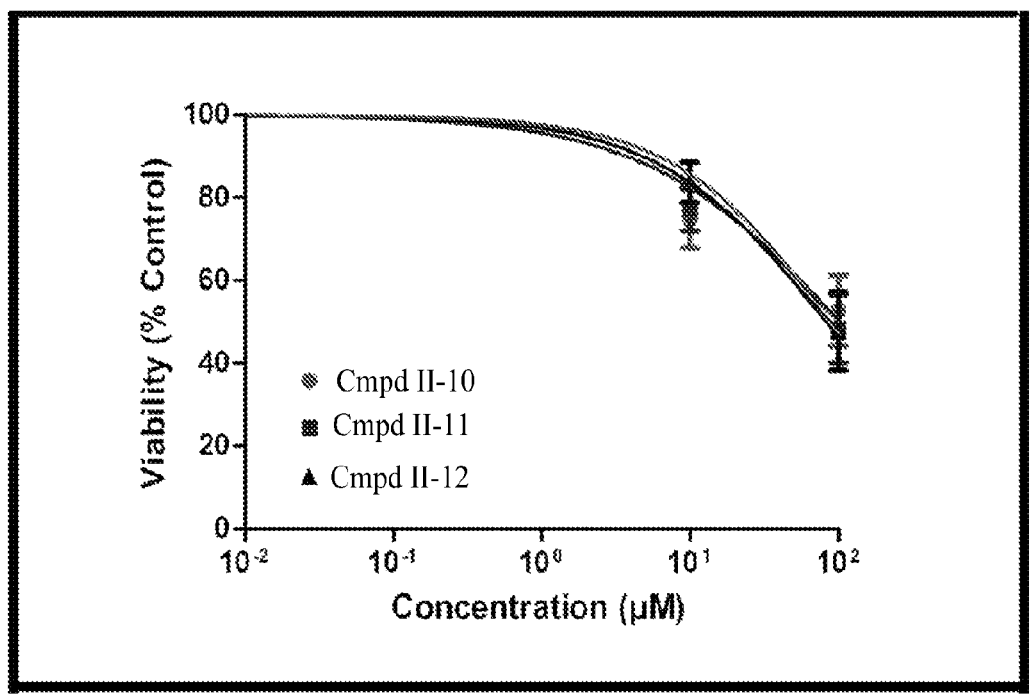
Figure 24:
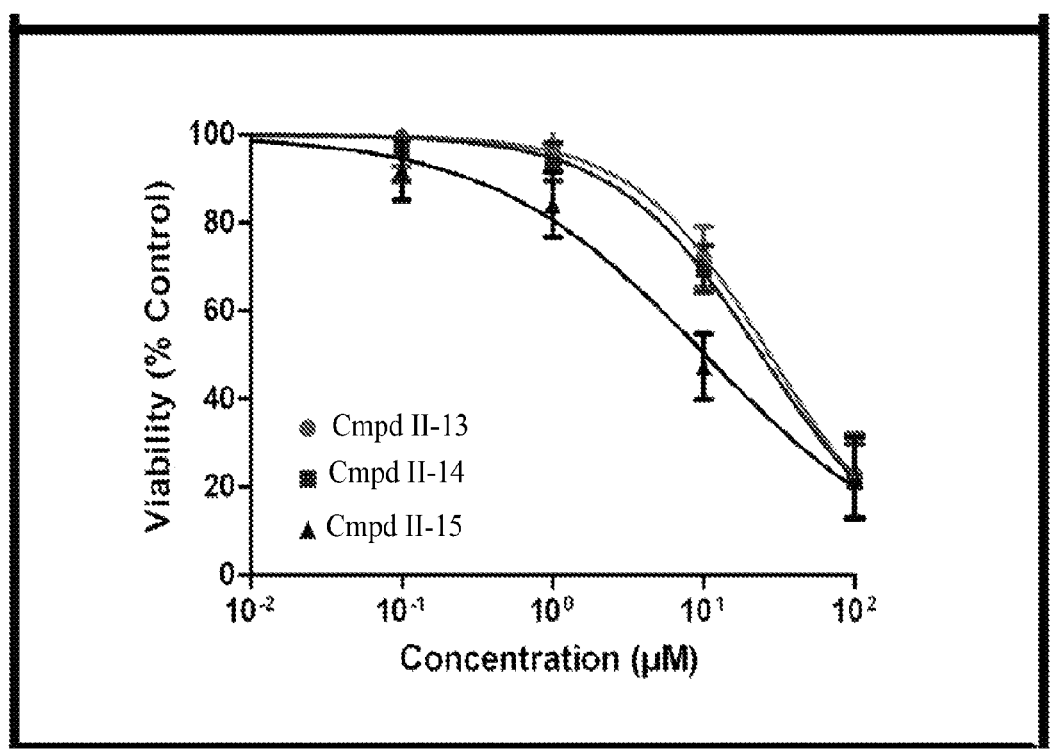
Figure 25:
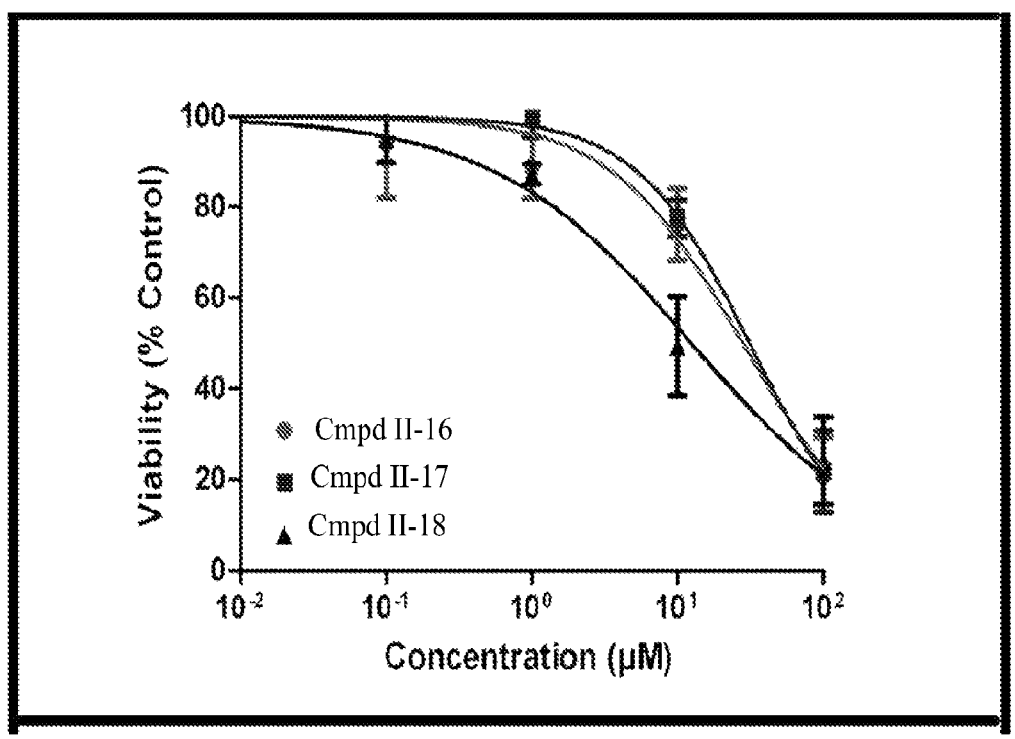
Figure 26:
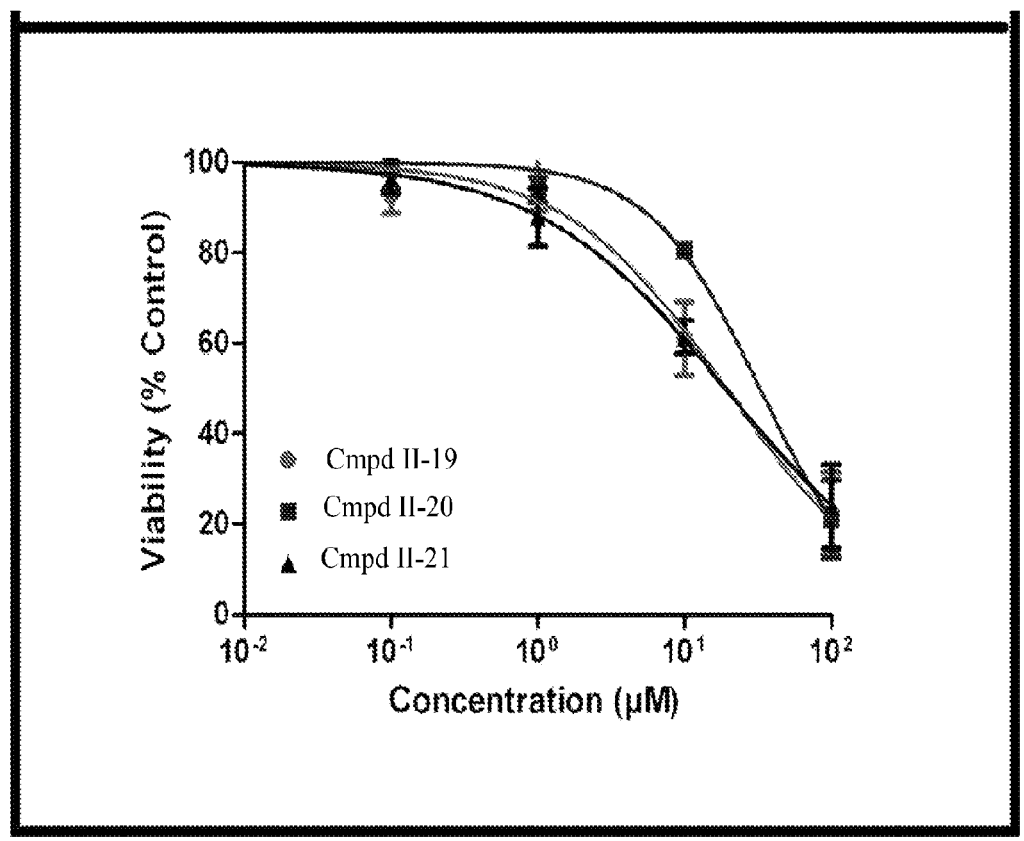
Figure 27:
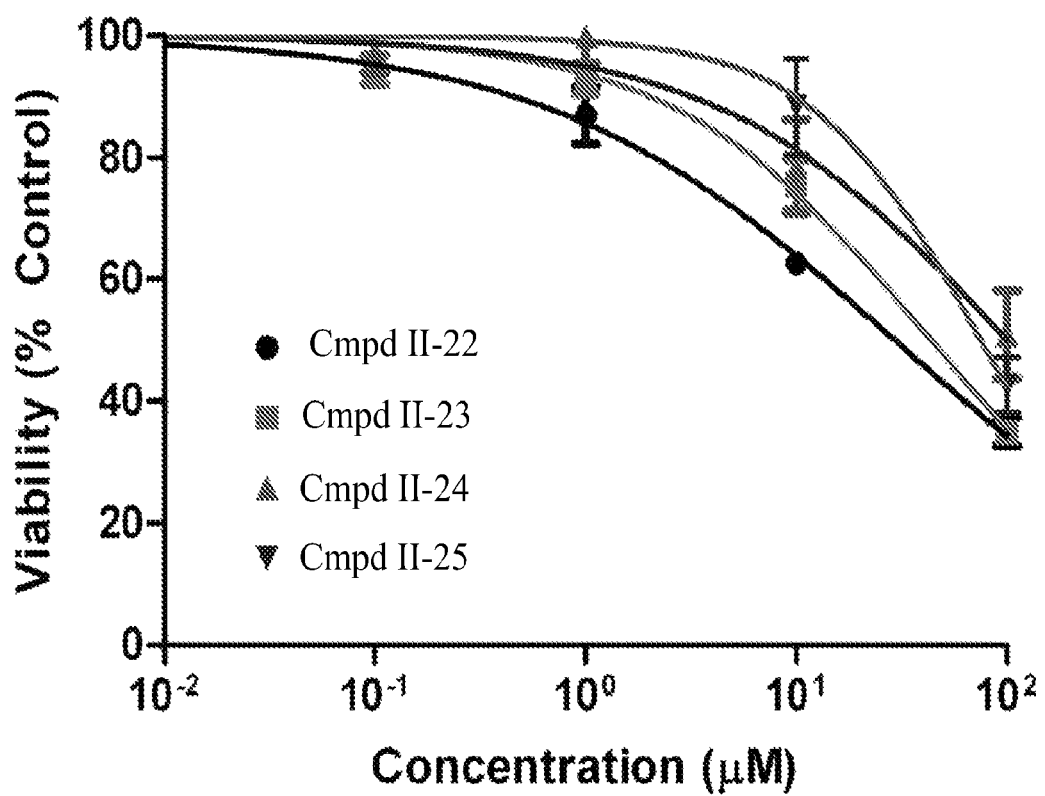

The effect of compound II-3 on endogenous sphingolipid levels was compared to C8-ceramide using Lipidomics Analysis (FIG. 19-21). Dihydrosphingosine is elevated following compound II-3 treatment, with almost a 50 fold increase in MCF-7TN-R cells. Sphingosine-1-phosphate, the proliferative metabolite of ceramide, decreased in all three cell lines. C8-ceramide had the opposite effect and increased sphingosine-1-phosphate levels. These results correlate with the increased potency of compound II-3 in reducing proliferation in MDA-MB-231 and MCF-7TN-R cells.

Nineteen compounds were synthesized using fifteen benzaldehydes as starting material. Five different substituents were incorporated into each position of the phenyl ring (ortho- (2-), meta- (3-), or para- (4-)) in order to determine the most effective combination of substituent and position. These were tested as potential anti-proliferative agents in MCF-7TN-R cells, and the structure-activity relationships were studied using several parameters. Table 3 shows compounds II-7 to II-21; FIGS. 22-27 show the results for II-7 to II-25. The results indicate that all compounds containing chloro-, methoxy-, and hydroxyl-substituents show greater efficacy. In compounds containing a methyl group, a significant increase of the PAC (C) in o-substituted compound was detected, which may account for the increased anti-proliferation activity. Ortho-substituted analogs with electron withdrawing groups by induction can have beneficial effects, and PAC (C) can be a useful predictor of the structural property of the molecule. While comparing imine and amine functional groups, it was found that the relatively high activity of the imine functional group may be due to the stability of the π-π conjugation at the hydrolytic site of the enzymes involved.

TABLE 3

| Compd. | Group | Position | MW | Log K | Log P (Predicted) | PAC (N) | PAC (C) | $IC_{50}$ (μM) |
|---|---|---|---|---|---|---|---|---|
| II-7  | —$NO_2$  | para-  | 433.5 | 0.86 | 5.59 | −0.2768 | 0.0295 | 216.5 |
| II-8  | —$NO_2$  | meta-  | 433.5 | 0.86 | 5.59 | −0.2768 | 0.0297 | 103.9 |
| II-9  | —$NO_2$  | ortho- | 433.5 | 0.88 | 5.56 | −0.2767 | 0.0337 | 21.71 |
| II-10 | —$CH_3$  | para-  | 402.6 | 1.09 | 6.37 | −0.2768 | 0.0295 | 101.5 |
| II-11 | —$CH_3$  | meta-  | 402.6 | 1.09 | 6.37 | −0.2768 | 0.0295 | 82.94 |
| II-12 | —$CH_3$  | ortho- | 402.6 | 1.09 | 6.20 | −0.2768 | 0.0298 | 87.71 |
| II-13 | —Cl      | para-  | 423.0 | 1.09 | 6.59 | −0.2768 | 0.0295 | 27.48 |
| II-14 | —Cl      | meta-  | 423.0 | 1.08 | 6.59 | −0.2768 | 0.0296 | 24.10 |
| II-15 | —Cl      | ortho- | 423.0 | 1.12 | 6.43 | −0.2768 | 0.0310 | 10.26 |
| II-16 | —$OCH_3$ | para-  | 418.6 | 0.91 | 5.94 | −0.2768 | 0.0295 | 28.13 |
| II-17 | —$OCH_3$ | meta-  | 418.6 | 0.92 | 5.94 | −0.2768 | 0.0296 | 31.25 |
| II-18 | —$OCH_3$ | ortho- | 418.6 | 0.89 | 5.96 | −0.2767 | 0.0322 | 12.50 |
| II-19 | —OH      | para-  | 404.5 | 0.73 | 5.67 | −0.2768 | 0.0295 | 19.33 |
| II-20 | —OH      | meta-  | 404.5 | 0.76 | 5.67 | −0.2768 | 0.0296 | 32.63 |
| II-21 | —OH      | ortho- | 404.5 | 0.89 | 5.70 | −0.2767 | 0.0322 | 18.97 |

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

Detailed descriptions of one or more embodiments are provided herein. It is to be understood, however, that the present invention may be embodied in various forms. Therefore, specific details disclosed herein (even if designated as preferred or advantageous) are not to be interpreted as limiting, but rather are to be used as a basis for the claims and as a representative basis for teaching one skilled in the art to employ the present invention in any appropriate manner.

What is claimed is:

1. A compound selected from the group consisting of

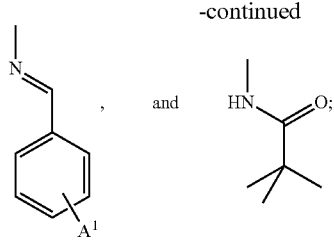

free bases, salts, optical isomers, geometric isomers, salts of isomers, ethers and esters of Formula (I) and Formula (II);

Where:
R$^1$ is selected from the group consisting of

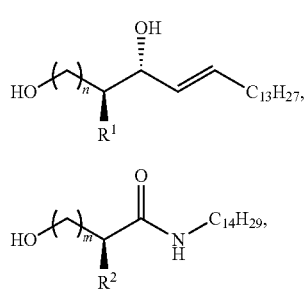

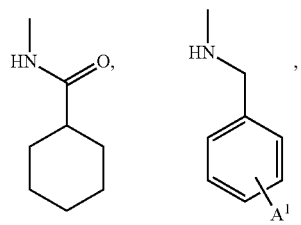

n is selected from the group consisting of 1, 2, and 3;
A$^1$ can be at the 2-, 3-, or 4-position of the ring, and is selected from the group consisting of —H, —$NO_2$, —$CH_3$, —$CH_2CH_3$, —$CH_2CH_2CH_3$, —$CHCH_3CH_3$, —Cl, —Br, —I, —$OCH_3$, —$OCH_2CH_3$, —CN, acyl groups, and —OH, wherein A$^1$ is not —$OCH_3$ in the 4-position;

R$^2$ is selected from the group consisting of

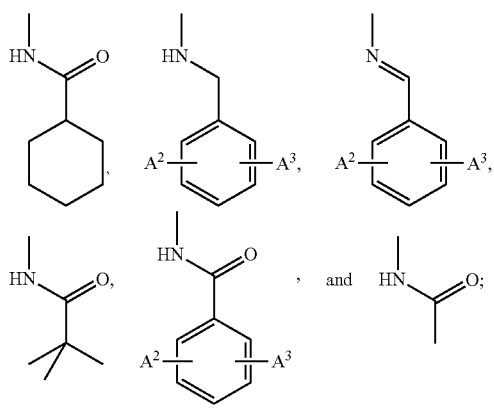

m is selected from the group consisting of 1, 2, and 3;
A$^2$ and A$^3$ can be the same or different, can be at the 2-, 3-, 4-, 5-, or 6-position of the ring, and are selected from the group consisting of —H, —$NO_2$, —$CH_3$, —$CH_2CH_3$, —$CH_2CH_2CH_3$, —$CHCH_3CH_3$, —Cl, —Br, —I, —$OCH_3$, —$OCH_2CH_3$, —CN, acyl groups, and —OH.

2. The compound of claim 1, wherein A$^2$ is in the 2-position and A$^3$ is in the 6-position.

3. The compound of claim 1, wherein A$^2$ is in the 2-position and A$^3$ is in the 6-position, and A$^2$ and A$^3$ are selected from electron withdrawing groups.

4. The compound of claim 1, wherein $A^2$ is in the 2-position and $A^3$ is in the 6-position, and $A^2$ and $A^3$ are selected from the groups consisting of —NO₂, —Cl, —Br, —I, —OCH₃, —OCH₂CH₃, —CN, acyl groups, and —OH.
5. The compound of claim 1, wherein n is 1.
6. The compound of claim 1, wherein m is 1.
7. The compound of claim 1, wherein the compound is selected from the group consisting of
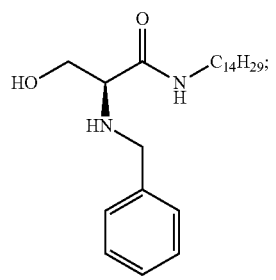
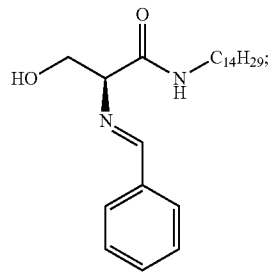
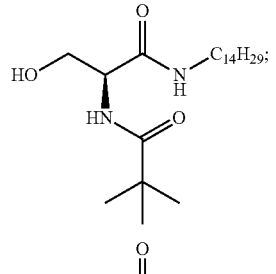
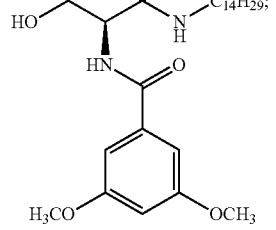
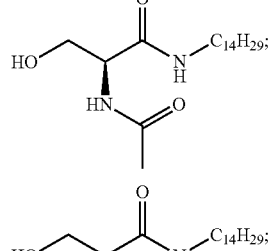
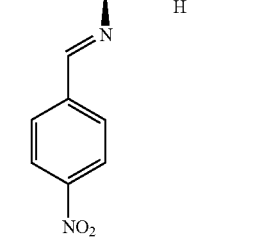

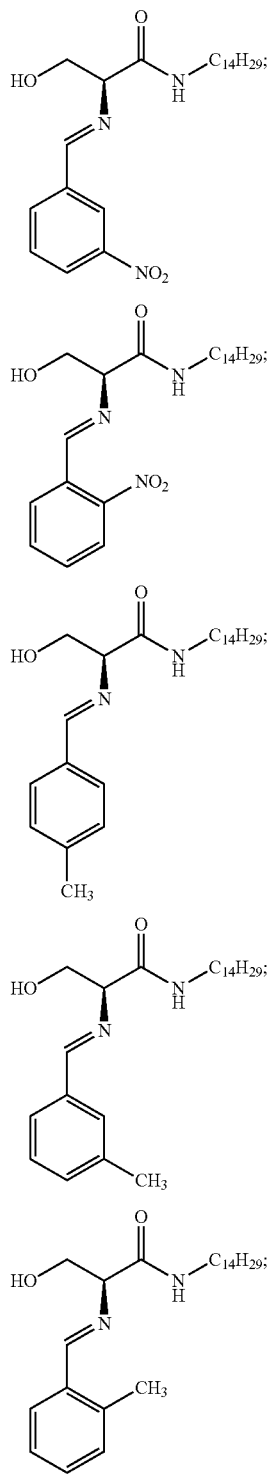
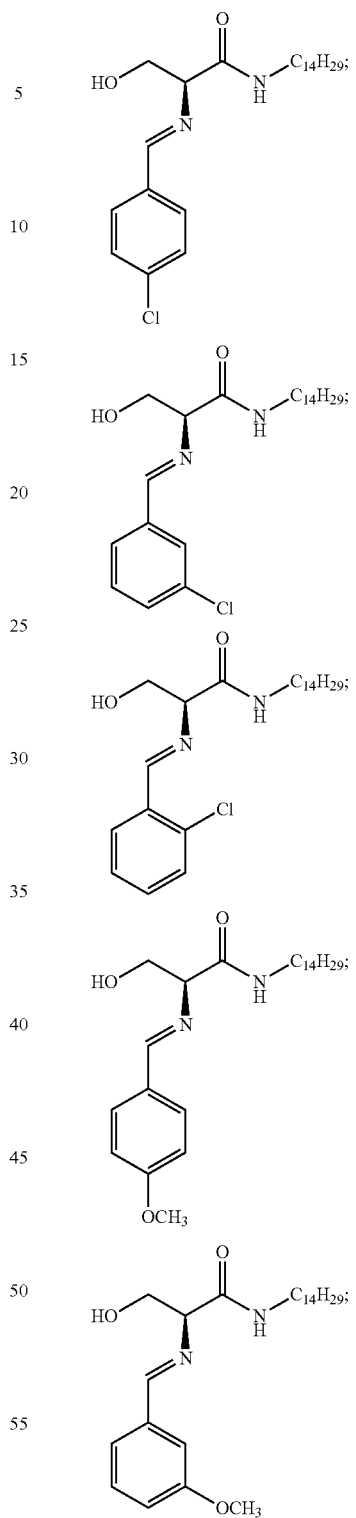

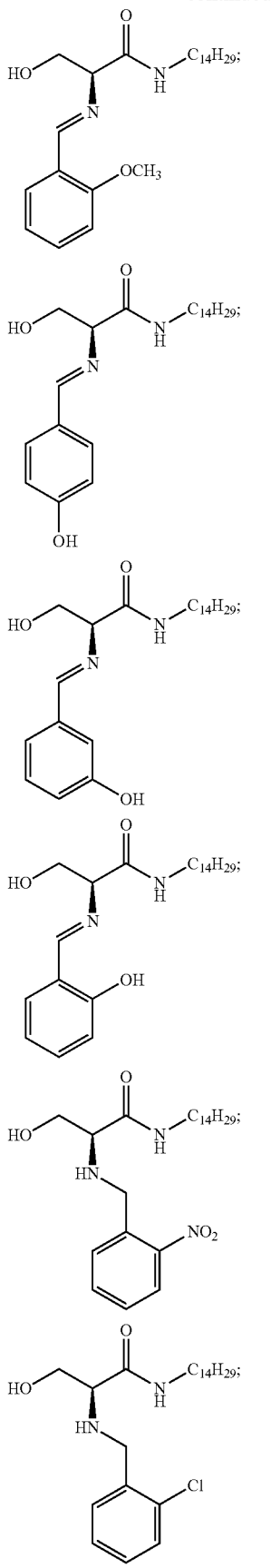

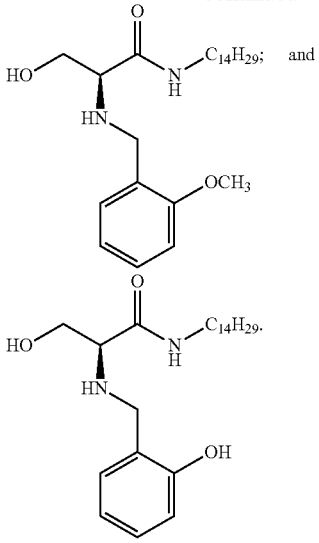

8. The compound of claim 1, wherein the compound is

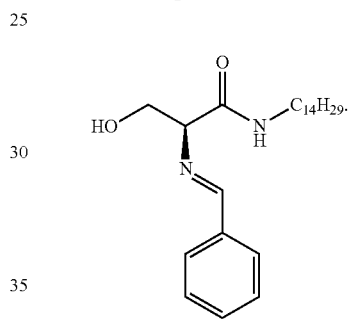

9. The compound of claim 1, wherein the $IC_{50}$ of the compound against a cancer cell determined by a clonogenic survival assay is not greater than about 20 μM.

10. The compound of claim 9, wherein the cancer cell is chemoresistant.

11. The compound of claim 9, wherein the cancer cell is MCF7-TN-R human breast cancer cell.

12. The compound of claim 9, wherein the $IC_{50}$ is not greater than about 10 μM and the cancer cell is chemoresistant.

13. A composition comprising the compound of claim 1.

14. A pharmaceutical composition comprising the compound of claim 1.

15. The pharmaceutical composition of claim 14, wherein the composition further comprises a liposome.

16. A method for synthesizing Formula (I) of claim 1 or its free base, salt, optical isomer, geometric isomer, salt of isomer, ethers or esters derivative comprising:
condensation of

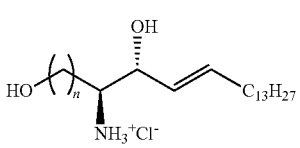

with an aldehyde or a carboxylic acid;
where n is selected from the group consisting of 1, 2, and 3.

17. The method of claim 16, wherein n=1.

18. The method of claim 16, wherein the condensation is of D-sphingosine with benzaldehyde.

19. The method of claim 16, wherein the method of synthesizing further comprises reduction by NaBH$_3$CN.

20. A method for synthesizing Formula (II) of claim 1 or its free base, salt, optical isomer, geometric isomer, salt of isomer, ethers or esters derivative comprising
condensation of

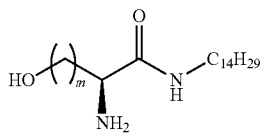

with an aldehyde or a carboxylic acid;
where m is selected from the group consisting of 1, 2, and 3.

21. The method of claim 20, wherein m=1.

22. The method of claim 20, wherein the condensation is of (S)-2-amino-3-hydroxy-N-tetradecylpropanamide with benzaldehyde.

23. The method of claim 20, wherein the method of synthesizing further comprises reduction by NaBH$_3$CN.

24. A method for treating cancer comprising
administering a compound of claim 1 to an animal
wherein the cancer is selected from the group consisting of breast cancer, kidney cancer, colon cancer, rectal cancer, ovarian cancer, stomach cancer, uterine cancer, carcinoma in situ, and leukemia.

25. The method of claim 24, wherein the animal is a mammal.

26. The method of claim 24, wherein the compound interferes with ceramidase in one or more cancer cells.

27. The method of claim 24, wherein the cancer is a tumor.

28. The method of claim 24, wherein the cancer is breast cancer or ovarian cancer.

29. The method of claim 24, wherein the compound is selected from Formula (II) and m=1.

30. The method of claim 24, wherein the compound is

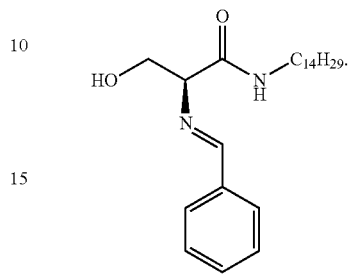

31. The method of claim 24, wherein the cancer is a chemoresistant cancer.

32. The method of claim 24, wherein the cancer is chemoresistant breast cancer or chemoresistant ovarian cancer.

33. The compound of claim 1, wherein A$^1$ can be at the 2-, 3-, or 4-position of the ring, and is selected from the group consisting of —H, —NO$_2$, —CH$_3$, —CH$_2$CH$_3$, —CH$_2$CH$_2$CH$_3$, —CHCH$_3$CH$_3$, —Cl, —Br, —I, —OCH$_2$CH$_3$, —CN, acyl groups, and —OH.

34. The compound of claim 1, wherein A$^1$ can be at the 2- or 3-position of the ring, and is selected from the group consisting of —H, —NO$_2$, —CH$_3$, —CH$_2$CH$_3$, —CH$_2$CH$_2$CH$_3$, —CHCH$_3$CH$_3$, —Cl, —Br, —I, —OCH$_3$, —OCH$_2$CH$_3$, —CN, acyl groups, and —OH.

* * * * *